(12) United States Patent
Oshima et al.

(10) Patent No.: US 10,619,011 B2
(45) Date of Patent: *Apr. 14, 2020

(54) ABSORBENT RESIN AND METHOD FOR PRODUCING THE SAME

(71) Applicant: NIPPON SHOKUBAI CO., LTD., Osaka-shi, Osaka (JP)

(72) Inventors: Kazuyuki Oshima, Himeji (JP); Yoshiro Mitsukami, Himeji (JP); Taku Fujimoto, Himeji (JP); Erina Minami, Himeji (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 92 days.

This patent is subject to a terminal disclaimer.

(21) Appl. No.: 15/321,544

(22) PCT Filed: Jun. 23, 2015

(86) PCT No.: PCT/JP2015/068083
§ 371 (c)(1),
(2) Date: Dec. 22, 2016

(87) PCT Pub. No.: WO2015/199089
PCT Pub. Date: Dec. 30, 2015

(65) Prior Publication Data
US 2017/0158826 A1 Jun. 8, 2017

(30) Foreign Application Priority Data

Jun. 23, 2014 (JP) ................................. 2014-127897
Aug. 28, 2014 (JP) ................................. 2014-174584

(51) Int. Cl.
| | | |
|---|---|---|
| A61F 13/49 | (2006.01) | |
| A61F 13/53 | (2006.01) | |
| A61L 15/26 | (2006.01) | |
| A61L 15/60 | (2006.01) | |
| C08G 81/02 | (2006.01) | |
| C08J 3/12 | (2006.01) | |
| C08J 3/24 | (2006.01) | |
| C08F 8/12 | (2006.01) | |
| B01J 20/26 | (2006.01) | |

(52) U.S. Cl.
CPC ............ *C08G 81/021* (2013.01); *A61F 13/49* (2013.01); *A61F 13/53* (2013.01); *A61L 15/26* (2013.01); *A61L 15/60* (2013.01); *B01J 20/267* (2013.01); *C08F 8/12* (2013.01); *C08J 3/12* (2013.01); *C08J 3/246* (2013.01); *B01J 2220/68* (2013.01); *C08G 2210/00* (2013.01); *C08J 2300/206* (2013.01); *C08J 2333/02* (2013.01); *C08J 2400/206* (2013.01)

(58) Field of Classification Search
CPC ........ A61F 13/49; A61F 13/532; A61L 15/26; A61L 15/60; B01J 20/267; B01J 2220/68; C08G 81/021; C08G 2210/00
See application file for complete search history.

(56) References Cited

U.S. PATENT DOCUMENTS

| | | | |
|---|---|---|---|
| 6,072,024 A | 6/2000 | Irizato et al. | |
| 10,172,971 B2 * | 1/2019 | Oshima | A61L 15/26 |
| 2007/0123658 A1 | 5/2007 | Torii et al. | |
| 2009/0208748 A1 | 8/2009 | Torii et al. | |
| 2009/0259016 A1 | 10/2009 | Johnson et al. | |
| 2009/0298685 A1 | 12/2009 | Torii et al. | |
| 2010/0308263 A1 | 12/2010 | Torii et al. | |
| 2012/0305842 A1 | 12/2012 | Torii et al. | |
| 2015/0367018 A1 * | 12/2015 | Oshima | A61L 15/26 604/372 |

FOREIGN PATENT DOCUMENTS

| | | |
|---|---|---|
| CN | 1272504 A | 11/2000 |
| CN | 102268127 A | 12/2011 |

(Continued)

OTHER PUBLICATIONS

International Preliminary Report on Patentability dated Jan. 5, 2017 which issued in the corresponding PCT Patent Application No. PCT/JP2015/068083.
Thomas L. Staples et al., Chemistry of Superabsorbent Polyacrylates, Modern Superabsorbent Polymer Technology (1998), pp. 55-60, pp. 97-103.
J. A. Johnson et al., J. et al., Synthesis of Degradable Model Networks via ATRP and Click Chemistry, Am. Chem. Soc., 2006, 128, pp. 6564-6565.
T. Sakai et al. et al., Design and Fabrication of a High-Strength Hydrogel with Ideally Homogeneous Network Structure from Tetrahedron-Like Macromonomers, Macromolecules, American Chemical Society 2008, 41, pp. 5379-5384.

(Continued)

*Primary Examiner* — Irina S Zemel
*Assistant Examiner* — Jeffrey S Lenihan
(74) *Attorney, Agent, or Firm* — Dickinson Wright PLLC

(57) ABSTRACT

A water-absorbing resin having a high swollen gel elastic modulus, a high swelling capacity and a method for producing the same are provided where the water-absorbing resin includes a water soluble unsaturated monomer having a dissociable group, an internal crosslinked structure index expressed by the following numerical formula of 14 or more, a weight average molecular weight (Mw) after a hydrolysis treatment of 220,000 or less, and a molecular weight distribution (Mw/Mn) after a hydrolysis treatment of 3.40 or less: Crosslinked structure index=(Equilibrium swelling capacity with respect to 0.9 wt % physiological saline solution$^{1/3}$/ (Weight average molecular weight (Mw) after hydrolysis treatment)×1000000; where the hydrolysis treatment leaves 50 mg of the water-absorbing resin as a solids content to stand still in 10 g of a 0.1 mol/l aqueous sodium hydroxide solution for 3 weeks at 80° C., and the weight average molecular weight (Mw) is measured after the treatment.

10 Claims, 1 Drawing Sheet

(56) References Cited

FOREIGN PATENT DOCUMENTS

| EP | 2130581 A1 | 9/2009 |
|---|---|---|
| JP | A-H10-324750 | 12/1998 |
| JP | A-2004-035639 | 2/2004 |
| JP | A-2005-111474 | 4/2005 |
| JP | A-2006-328346 | 12/2006 |
| JP | A-2009-114414 | 5/2009 |
| JP | A-2009-531467 | 9/2009 |
| JP | A-2012-012462 | 1/2012 |
| WO | WO2008/016371 A1 | 2/2008 |

OTHER PUBLICATIONS

International Search Report and Written Opinion dated Oct. 13, 2015 which issued in PCT Application No. PCT/JP2015/068083.
Japanese Official Notice of Reason for Refusal dated Sep. 12, 2017 which issued in the corresponding Patent Application No. 2016-529608, including English translation.
European Office Action dated Nov. 30, 2018, which issued in the corresponding Patent Application No. 15 811 294.6.

* cited by examiner

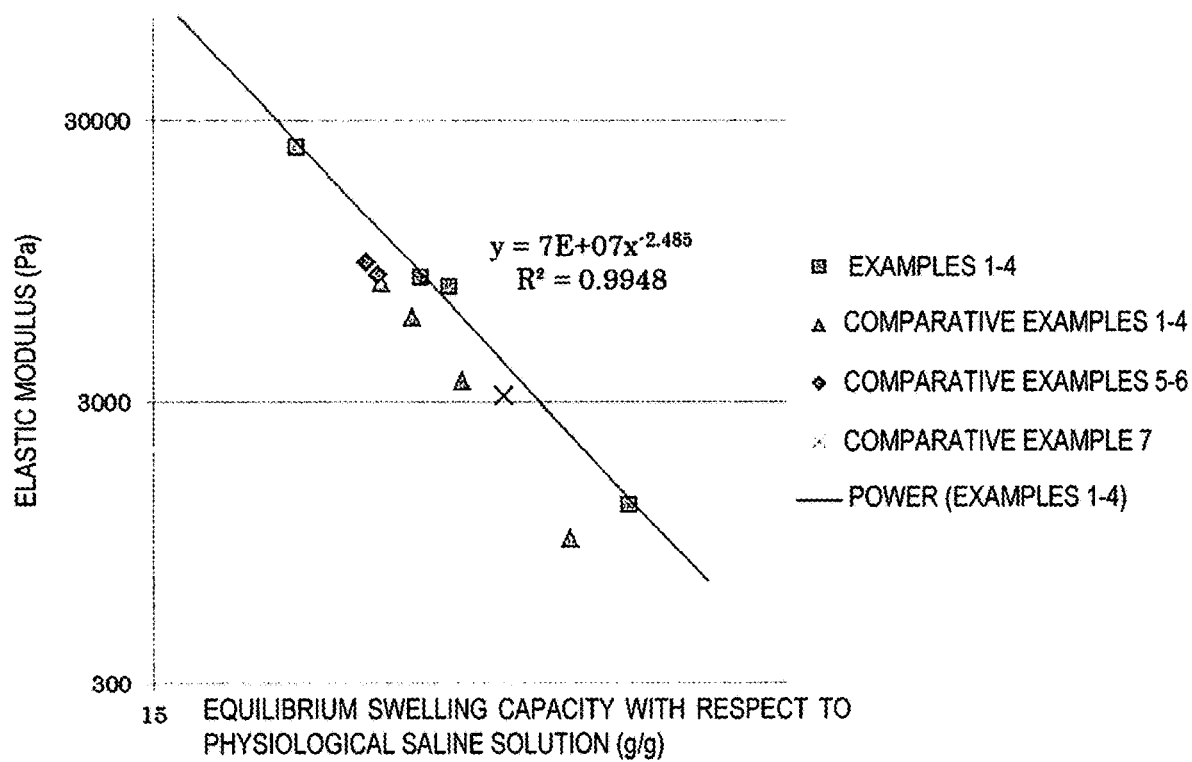

ABSORBENT RESIN AND METHOD FOR PRODUCING THE SAME

JOINT RESEARCH AGREEMENT

The claimed invention was made by a joint research agreement between the applicant Nippon Shokubai Co. Ltd, at Kogin Bldg. 4-1-1 Koraibashi, Chu-ku, Osaka, Japan and The Procter & Gamble Company at One Procter & Gamble Plaza, Cincinnati, Ohio 45202. The joint research agreement was in effect on or before the effective filing date of the claimed invention, and the claimed invention was made as a result of activities undertaken within the scope of the joint research agreement.

TECHNICAL FIELD

The present invention relates to a water-absorbing resin that can be used in an absorbent article such as disposable diapers, sanitary napkins, and the so-called incontinence pads and a method for producing the same.

BACKGROUND ART

Hitherto, a water-absorbing resin has been used as one of the constituent materials of sanitary cotton, disposable diapers, or other hygienic materials that absorb body fluids. As such a water-absorbing resin, for example, there are a hydrolysate of a starch-acrylonitrile graft polymer, a neutralized product of a starch-acrylic acid graft polymer, a saponified product of a vinyl acetate-acrylic acid ester copolymer, a hydrolysate of an acrylonitrile copolymer or an acrylamide copolymer, a crosslinked body thereof, and a partially neutralized poly(meth)acrylic acid crosslinked body. Among them, a water-absorbing resin formed from a partially neutralized polyacrylic acid (salt) crosslinked body is often used from the viewpoint of the absorbing properties. These all have a crosslinked structure and are insoluble in water.

The properties desired for such a water-absorbing resin include a high fluid retention capacity, a high water absorption speed, an excellent suction power to suck up water from a base material, high liquid permeability, and the like. Among these, liquid permeability of a water-absorbing resin is understood as the ability to transport the liquid added within the particles or between the particles and to three-dimensionally distribute the liquid in the swollen state thereof. In the case of particulate water-absorbing resin, the transport by a capillary action through the gap between the gel particles of the swollen water-absorbing resin is dominant. Hitherto, in a water-absorbing resin that cannot maintain the capillary voids by the gel alone under a load due to the lack of stability of the gel, the mutual separation between the particles is secured by holding these materials in a fiber matrix. However, in the structure of diapers of the new generation, a fibrous material for supporting the liquid transport by the water-absorbing resin is used only in a small amount or not used at all. Hence, the water-absorbing resin used therein is required to have sufficiently high stability in the swollen state. A water-absorbing resin is required to have a swollen gel elastic modulus in order to achieve high stability in the swollen state.

For the purpose of improving various kinds of absorption properties such as a swollen gel elastic modulus of the water-absorbing resin, an operation to form a crosslinked structure in the vicinity of the surface of the water-absorbing resin by using a crosslinking agent having a plurality of functional groups capable of reacting with a carboxyl group present in the water-absorbing resin and thus to increase the surface crosslinking density of the water-absorbing resin (surface crosslinking) has been hitherto conducted (Modern Superabsorbent Polymer Technology, 1998, pp. 55-60 and pp. 97-103). In addition, when a partially neutralized polyacrylic acid internally crosslinked body (base polymer) is synthesized before the surface crosslinking as well, it is conducted to improve the swollen gel elastic modulus by a technique to add a chain transfer agent at the time of polymerization (JP 2005-111474 A) or a technique to increase the amount of a radical initiator to be used at the time of polymerization (JP2009-531467 W). The mechanism of the improvement of the swollen gel elastic modulus by these techniques is considered to be as follows. That is, it is possible to lower the weight average molecular weight of the main chain polymer in the water-absorbing resin by adding a chain transfer agent or increasing the amount of a radical initiator at the time of polymerization. Due to this, entangled crosslinkings of the main chain polymer decrease. The entangled crosslinkings suppress the swelling of gel. Hence, in a case when a chain transfer agent is added or the amount of a radical initiator is increased at the time of polymerization, it is required to compensate the decrease in entangled crosslinkings with chemical crosslinking by increasing the amount of an internal crosslinking agent to be used in order to obtain a water-absorbing resin having an equal equilibrium absorption capacity as a water-absorbing resin obtained by normal polymerization. As a result, in the water-absorbing resin obtained by these techniques, the proportion of the entangled crosslinkings in the internal crosslinked structure becomes lower and the proportion of chemical crosslinking becomes higher as compared to a water-absorbing resin obtained by normal polymerization. It is considered to be important that the proportion of chemical crosslinking is higher in this way, in order to achieve a high swollen gel elastic modulus.

However, a great difference in weight average molecular weight of the main chain between the water-absorbing resin obtained by these techniques and a normal water-absorbing resin, and the amount of a chemical crosslinking agent for achieving an equal equilibrium absorption capacity is also not significantly different. Hence, it is considered that a great number of entangled crosslinkings are still present even in the crosslinked structure of the water-absorbing resin obtained by these techniques, and it is thought that there is room for significant improvement.

Note that, here, it is considered that the achievement of a high swollen gel elastic modulus cannot be expected by only decreasing the proportion of entangled crosslinkings by simply further decreasing the weight average molecular weight of the main chain. This is because it is considered that it is required not only to decrease the weight average molecular weight of the main chain but also to narrow the molecular weight distribution of the main chain at the same time for the reasons as described below in order to achieve a high swollen gel elastic modulus. That is, in the case of a water-absorbing resin having a small weight average molecular weight of the main chain and a wide molecular weight distribution, a great number of significantly short main chains are present in the crosslinked structure thereof. The number of crosslinking points contained in such a significantly short main chain is considered probabilistically significantly small. In a case when the crosslinking points are fewer, the proportion of the length of a dangling chain to the total chain length is increased. The dangling chain here refers to a terminal portion of the main chain that is not sandwiched between a crosslinking point and another crosslinking point. In an extreme case, the main chain that has only one crosslinking point is a dangling chain in its entirety. Since a dangling chain does not contribute to the swollen gel elastic modulus, it is preferable to decrease the dangling chains and increase the main chains that are effective in the elastic modulus in order to improve the swollen gel elastic modulus. Accordingly, it is considered that it is required to prevent the generation of significantly short main chains by narrowing the molecular weight distribution of the main chain in order to suppress the generation of dangling chains.

From the matters described above, it is considered that the entangled crosslinkings or dangling chains present in the crosslinked structure can be significantly decreased and it can be expected to have a high swollen gel elastic modulus if it is possible to obtain a water-absorbing resin having a small weight average molecular weight of the main chain, a narrow molecular weight distribution of the main chain, and a uniform network structure with a uniform mesh size.

Hitherto, studies on the synthesis of a gel having a uniform network structure with a uniform mesh size have been carried out, and for example, a technique to synthesize a polyacrylic acid ester crosslinked body having a uniform network structure by crosslinking the terminal of a straight-chain polymer having a functional group at both terminals with a star-shaped low molecule is disclosed in J. A. Johnson at al., J. Am. Chem. Soc., 2006, 128, pp. 6564-6565. In addition, whereas the disclosure of J. A. Johnson et al., J. Am. Chem. Soc., 2006, 128, pp. 6564-6565 mostly relates to a polyacrylic acid ester crosslinked body, it is described that "this polyacrylic acid ester crosslinked body can be converted to a polyacrylic acid crosslinked body."

In addition, with regard to the "synthesis of a nonionic hydrophilic gel having a uniform network structure", there are numerous known literatures relating to the synthesis of a polyethylene glycol crosslinked body through a reaction of two kinds of star-shaped polymers and the evaluation on physical properties thereof (for example, T. Sakai et al., Macromolecules, 2008, 41, pp. 5379-5384).

Note that, in the prior arts relating to the "synthesis of a gel having a uniform network structure" such as J. A. Johnson et al., J. Am. Chem. Soc., 2006, 128, pp. 6564-6565 and T. Sakai et al., Macromolecules, 2008, 41, pp. 5379-5384, it is not disclosed at all to form an ionic network structure by reacting two or more kinds of star-shaped polymers.

SUMMARY OF INVENTION

It has been revealed through the investigations by the present inventors that, in the technique which was proposed in the prior art and attempted the improvement of the swollen gel elastic modulus by controlling the production conditions when producing the base polymer before the surface crosslinking, there is a problem that the swelling capacity required for a water-absorbing resin in the first place significantly decreases when it is tried to increase the swollen gel elastic modulus.

Accordingly, an object of the present invention is to provide a water-absorbing resin capable of having a high swollen gel elastic modulus while maintaining a high swelling capacity and a method for producing the same.

The present inventors have carried out intensive investigations in view of the above problems, and as a result, they have found out that the above problems can be solved by controlling the value of an equilibrium swelling capacity of a water-absorbing resin which contains a water soluble unsaturated monomer having a dissociable group as a main component of a repeating unit of a main chain and has an internal crosslinked structure with respect to physiological saline solution, the value of a weight average molecular weight (Mw) of the water-absorbing resin after a predetermined hydrolysis treatment, and the molecular weight distribution (Mw/Mn) of the water-absorbing resin so that they satisfy a predetermined relationship, thereby completing the present invention.

That is, according to an aspect of the present invention, provided is a water-absorbing resin which contains a water soluble unsaturated monomer having a dissociable group as a main component of a repeating unit of a main chain and has an internal crosslinked structure, wherein the water-absorbing resin has a crosslinked structure index expressed by the following numerical formula 1 is 14 or more, a weight average molecular weight (Mw) of the water-absorbing resin after a hydrolysis treatment is 220,000 or less, and a molecular weight distribution (Mw/Mn) of the water-absorbing resin after a hydrolysis treatment is 3.40 or less.

[Math. 1]

$$\text{Crosslinked structure index} = \frac{(\text{Equilibrium swelling capacity with respect to 0.9 wt \% physiological seine solution})^{1/3}}{(\text{Weight average molecular weight (Mw) after hydrolysis treatment})} \times 1000000$$

[Numerical formula 1]

Where the hydrolysis treatment is a treatment to leave 50 mg of the water-absorbing resin as a solids content to stand still in 10 g of a 0.1 mol/l aqueous sodium hydroxide solution for 3 weeks at 80° C., and the weight average molecular weight (Mw) is a value measured after the treatment.

In addition, the present inventors have found out a method that is completely different from a method for producing a partially neutralized polyacrylic acid (salt) crosslinked body which has been generally used in the prior art as one of the methods for producing a water-absorbing resin capable of exerting excellent properties (a high elastic modulus while maintaining the equilibrium swelling capacity) as described above.

That is, according to another aspect of the present invention, a method for producing a water-absorbing resin which contains a water soluble unsaturated monomer having a dissociable group as a main component of a repeating unit of a main chain and has an internal crosslinked structure is provided. The production method according to this aspect is characterized by including a reaction step for reacting a first star-shaped polymer which contains the water soluble unsaturated monomer as a main component of a repeating unit of each branched chain and has a first reactive functional group at a terminal of each branched chain with a second star-shaped polymer which contains the water soluble unsaturated monomer as a main component of a repeating unit of each branched chain and has a second reactive functional group capable of forming a chemical bond with the first reactive functional group by reacting with each other at a terminal of each branched chain.

According to the present invention, a water-absorbing resin capable of having a high swollen gel elastic modulus while maintaining a high swelling capacity and a method for producing the same are provided.

BRIEF DESCRIPTION OF DRAWINGS

FIG. 1 is a graph (origin is an equilibrium swelling capacity of 15 g/g and an elastic modulus of 300 Pa) plotted by taking the measured equilibrium swelling capacity as the horizontal axis and the logarithm of the elastic modulus (Pa) as the vertical axis for the water-absorbing resins produced in Example and Comparative Examples.

DESCRIPTION OF EMBODIMENTS

Hereinafter, the present invention will be described in detail, but the scope of the present invention is not bound by these descriptions, and embodiments other than the following examples may be implemented by being appropriately modified without departing from the gist of the present invention.

[1] Definition of Terms (1-1) Water-Absorbing Resin

In the present specification, the term "water-absorbing resin" means a water swellable and water insoluble polymer gelling agent. Incidentally, the term "water swellable" means that CRC (absorption capacity without pressure) defined in ERT441.2-02 is 5 [g/g] or more, and the term "water insoluble" means that Extr (water soluble component) defined in ERT470.2-02 is from 0 to 50 mass %. Here, the shape of the water-absorbing resin is preferably a powdery shape, the water-absorbing resin is particularly preferably a powdery water-absorbing resin having the particle size and moisture content to be described later, and it is referred to as a water-absorbing resin particle. Incidentally, in the present specification, the "water-absorbing resin" includes a water-swollen gel of the polymer gelling agent described above.

(1-2) [EDANA] and [ERT]

"EDANA" is the abbreviation of the European Disposables and Nonwovens Associations, "ERT" is the abbreviation of the measuring method (EDANA Recommended Test Methods) of a water-absorbing resin, which is a European standard. Incidentally, in the present invention, the physical properties of the water-absorbing resin are measured in conformity to the ERT original text (known publication: revised in 2002) unless otherwise stated. In addition, when the measurement is conducted for the following (a) to (d) described below, it is preferable to conduct the measurement after obtaining a dry polymer through a drying step described later in a case in which the water-absorbing resin is a water-swollen gel.

(a) [CRC] (ERT441.2-02)

"CRC" is the abbreviation of the Centrifuge Retention Capacity, and it means the absorption capacity without pressure (hereinafter, referred to as the "absorption capacity" in some cases). Specifically, it is the absorption capacity (unit: [g/g]) after 0.200 g of the water-absorbing resin in a nonwoven fabric is subjected to free swelling in an excess amount of a 0.9 wt % aqueous sodium chloride solution (physiological saline solution) for 30 minutes and then drained at 250 G by using a centrifuge.

(b) [AAP] (ERT442.2-02)

"AAP" is the abbreviation of the Absorption Against Pressure, and it means the absorption capacity under pressure. Specifically, it is the absorption capacity (unit: [g/g]) after 0.900 g of the water-absorbing resin is swollen in a 0.9 wt % aqueous sodium chloride solution (physiological saline solution) for one hour under a load of 2.06 kPa (0.3 psi).

(c) [SFC]

"SFC (Saline Flow Conductivity)" means the liquid permeability of a 0.69 wt % aqueous sodium chloride solution with respect to the water-absorbing resin under a load of 2.07 kPa, and it is measured in conformity to the SFC test method disclosed in U.S. Pat. No. 5,669,894.

(d) [PSD] (ERT420.2-02)

"PSD" is the abbreviation of Particle Size Distribution, and it means the particle size distribution measured by sieve classification. Incidentally, the mass average particle diameter (D50) and the width of the particle size distribution are measured by the same methods as the "Average Particle Diameter and Distribution of Particle Diameter" described in European Patent No. 0349240.

(1-3) Others

In the present specification, the term "X to Y" which indicates a range means the term "X or more and Y or less" including X and Y. In addition, the term "t (ton)" of a unit of mass means the term "metric ton", and the term "ppm" means the term "mass ppm" unless otherwise stated. In addition, the term "-acid (salt)" means the term "-acid and/or a salt thereof", and the term "(meth)acryl" means the term "acryl and/or methacryl." In addition, with regard to the measurement of physical properties and the like, the measurement is conducted at room temperature (20 to 25° C.) and a relative humidity of from 40 to 50% RH unless otherwise stated.

[2] Water-Absorbing Resin According to the Present Invention

According to an aspect of the present invention, a water-absorbing resin which contains a water soluble unsaturated monomer having a dissociable group as a main component of a repeating unit of a main chain and has an internal crosslinked structure is provided. Moreover, the water-absorbing resin according to the aspect is characterized in that the crosslinked structure index expressed by a numerical formula 1 described later is 14 or more, the weight average molecular weight (Mw) of the water-absorbing resin after a hydrolysis treatment is 220,000 or less, and the molecular weight distribution (Mw/Mn) of the water-absorbing resin after a hydrolysis treatment is 3.40 or less.

(2-1) Configuration of Water-Absorbing Resin

The water-absorbing resin according to the present aspect contains a water soluble unsaturated monomer having a dissociable group as a main component of the repeating unit of a main chain. Here, in the present specification, the fact that a monomer is "a main component of the repeating unit" means that the proportion of the monomer in the entire repeating unit is 50 mol % or more, and the proportion is preferably 70 mol % or more, more preferably 90 mol % or more, even more preferably 95 mol % or more, particularly preferably 98 mol % or more, and most preferably 99 mol % or more unless otherwise stated.

The "water soluble unsaturated monomer having a dissociable group" is preferably one that contains (meth)acrylic acid (salt) as the main component and more preferably one that contains acrylic acid (salt) as the main component. Examples of the (meth)acrylic acid salt may include an alkali metal salt such as a sodium salt, a potassium salt, or a lithium salt, an ammonium salt, and an amine salt of (meth)acrylic acid, and it is preferably an alkali metal salt of (meth)acrylic acid and most preferably a sodium salt of (meth)acrylic acid.

Examples of a monomer that can be used other than (meth)acrylic acid (salt) as the "water soluble unsaturated monomer having a dissociable group" may include an anionic unsaturated monomer such as maleic acid, vinylsulfonic acid, styrenesulfonic acid, 2-(meth)acrylamide-2-methylpropanesulfonic acid, 2-(meth)acryloylethanesulfonic acid, or 2-(meth)acryloylpropanesulfonic acid.

The water-absorbing resin according to the present aspect contains a water soluble unsaturated monomer having a dissociable group as the main component of the repeating unit of the main chain as described above, but it may have a "water soluble unsaturated monomer which does not have a dissociable group" as a repeating unit of the main chain. Examples of such a monomer may include nonionic hydrophilic group-containing unsaturated monomers such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono (meth)acrylate, vinylpyridine, N-vinylpyrrolidone, N-acryloyl piperidine, N-acryloylpyrrolidine, and N-vinylacetamide; and cationic unsaturated monomers such as N, N-dimethylaminoethyl (meth)acrylate, N, N-diethylaminoethyl (meth)acrylate, N,N-dimethylaminopropyl (meth)acrylate, N,N-dimethylaminopropyl (meth)acrylamide, and any quaternary salt of these.

Here, the water soluble unsaturated monomer described above may be used singly or two or more kinds thereof may be used by being appropriately mixed.

In the water-absorbing resin according to the present aspect, among the repeating units of the main chain, the proportion of the repeating unit derived from a water soluble unsaturated monomer having a carboxylic acid (salt) group as a dissociable group is preferably 70 mol % or more, more preferably 80 mol % or more, and even more preferably 90 mol % or more (the upper limit value is 100 mol %). Among the repeating units of the main chain, the proportion of the repeating unit derived from acrylic acid (salt) is preferably 70 mol % or more, more preferably 80 mol % or more, and even more preferably 90 mol % or more (the upper limit value is 100 mol %). Furthermore, as the constituent unit of the repeating unit of the main chain of the water-absorbing resin, one in which acrylic acid is in a range of from 0 to 50 mol % and an acrylic acid salt is in a range of from 100 to 50 mol % (the total amount of both is 100 mol % or less) is preferable and one in which acrylic acid is in a range of from 10 to 40 mol % and an acrylic acid salt is in a range of from 90 to 60 mol % (the total amount of both is 100 mol % or less) is more preferable. Incidentally, the molar ratio of the acrylic acid salt to the total amount of this acrylic acid and the acrylic acid salt is referred to as the "rate of neutralization." The value of this rate of neutralization is preferably from 50 to 100 mol %.

The water-absorbing resin according to the present aspect is a crosslinked polymer having an internal crosslinked structure. As a method for introducing the internal crosslinked structure into the water-absorbing resin according to the present aspect, a method to react two (or more) kinds of star-shaped polymers which contain a water soluble unsaturated monomer providing the repeating unit of the main chain of the water-absorbing resin as a main component of the repeating unit of the branched chain and have functional groups reactive to each other at the terminal of the branched chain is exemplified as described later in detail in the section for the "method for producing a water-absorbing resin" according to another aspect of the present invention.

(2-2) Crosslinked Structure Index

The water-absorbing resin according to the present aspect is characterized in that the crosslinked structure index expressed by the following numerical formula 1 is 14 or more, the weight average molecular weight (Mw) of the water-absorbing resin after a hydrolysis treatment is 220,000 or less, and the molecular weight distribution (Mw/Mn) of the water-absorbing resin after a hydrolysis treatment is 3.40 or less:

[Math. 2]

$$\text{Crosslinked structure index} = \text{(Equilibrium swelling capacity with respect to 0.9 wt \% physiological saline solution)}^{1/3}/\text{(Weight average molecular weight (Mw) after hydrolysis treatment)} \times 100000 \quad \text{[Numerical formula 1]}$$

Here, the hydrolysis treatment is a treatment to leave 50 mg of the water-absorbing resin as a solids content to stand still in 10 g of a 0.1 mol/l aqueous sodium hydroxide solution for 3 weeks at 80° C., the weight average molecular weight (Mw) is a value measured after the treatment, and the operation for this measurement will be described later in detail in the section for Examples.

It is essential that this crosslinked structure index be 14 or more, but it is preferably 30 or more, more preferably 60 or more, even more preferably 90 or more, particularly preferably 120 or more, and most preferably 170 or more. The upper limit value of the crosslinked structure index is not particularly limited, but it is preferably 1,000 or less. When the crosslinked structure index is greater than 1,000, there is a risk that the cost for the production of the water-absorbing resin increases too high. In addition, it is essential that the weight average molecular weight (Mw) of the water-absorbing resin after the hydrolysis treatment described above be 220,000 or less, but it is preferably 150,000 or less, more preferably 100,000 or less, even more preferably be 50,000, and particularly preferably 25,000 or less. The lower limit value of the weight average molecular weight (Mw) of the water-absorbing resin after the hydrolysis treatment is not particularly limited, but it is preferably 10,000 or more. When the weight average molecular weight (Mw) of the water-absorbing resin after the hydrolysis treatment is less than 10,000, there is a risk that the cost for the production of the water-absorbing resin increases too high. Furthermore, it is essential that the molecular weight distribution (Mw/Mn) of the water-absorbing resin after the hydrolysis treatment be 3.40 or less, but it is preferably 2.50 or less, more preferably 1.80 or less, even more preferably 1.45 or less, and particularly preferably 1.15 or less (the lower limit value is 1.00). According to the investigations by the present inventors, it has been found out that a water-absorbing resin having a high swollen gel elastic modulus while maintaining a high swelling capacity is provided as this crosslinked structure index is 14 or more, the weight average molecular weight (Mw) after the hydrolysis treatment is 220,000 or less, and the molecular weight distribution (Mw/Mn) after the hydrolysis treatment is 3.40 or less. As the mechanism for that, the above effect is exerted by having the configuration according to the present invention, the following one is presumed. That is, the fact that the crosslinked structure index is not less than a predetermined value means that the equilibrium swelling capacity is great and the weight average molecular weight is small, and it indicates that the entangled crosslinkings are fewer. In addition, the fact that the molecular weight distribution is narrow indicates that the significantly short main chains are fewer and the proportion of dangling chains is low. As described in the section for the "Background Art", it is considered that the swollen gel elastic modulus increases as the proportion of entangled crosslinkings is low and the proportion of chemical crosslinkings is high and as the dangling chains which do not contribute to the elasticity of gel are fewer in a case in which water-absorbing resins having an equal equilibrium absorption capacity are compared to each other. Hence, when the crosslinked structure index is 14 or more, the weight average molecular weight (Mw) after the hydrolysis treatment is 220,000 or less, and the molecular weight distribution (Mw/Mn) after the hydrolysis treatment is 3.40 or less, a water-absorbing resin which has fewer entangled crosslinkings and dangling chains and has a high swollen gel elastic modulus while maintaining a high swelling capacity is obtained. Incidentally, the operations for the measurement of these parameters will be described later in detail in the section for Examples.

[3] Method for Producing Water-Absorbing Resin According to the Present Invention (3-1) Overview According to another aspect of the present invention, an example of the method for producing [2] the water-absorbing resin according to the present invention described above is also provided. That is, the technical scope of the invention according to [2] the water-absorbing resin according to the present invention described above is not limited to those produced by the production method described in detail below.

As described above, as an example of the method for producing a water-absorbing resin according to the present invention, a method to react two kinds (or more) of star-shaped polymers which contain a water soluble unsaturated monomer providing the repeating unit of the main chain of the water-absorbing resin as a main component of the repeating unit of the branched chain and have functional groups reactive to each other at the terminal of the branched chain is exemplified.

That is, according to another aspect of the present invention, a method for producing a water-absorbing resin which contains a water soluble unsaturated monomer having a dissociable group as a main component of a repeating unit of a main chain and has an internal crosslinked structure is provided. In addition, the production method is characterized by including a reaction step for reacting a first star-shaped polymer which contains the water soluble unsaturated monomer as a main component of a repeating unit of each branched chain and has a first reactive functional group at a terminal of each branched chain with a second star-shaped polymer which contains the water soluble unsaturated monomer as a main component of a repeating unit of each branched chain and has a second reactive functional group capable of forming a chemical bond with the first reactive functional group by reacting with each other at a terminal of each branched chain.

(3-2) Reaction Step

This step is for reacting the first star-shaped polymer with the second star-shaped polymer. Incidentally, three or more kinds of the star-shaped polymers may be reacted in the reaction step in some cases. Here, the term "star-shaped polymer" means a branched polymer having a structure in which three or more branched chains are radially extended from an atom or an atomic group as a core. Incidentally, with regard to the "star-shaped polymer", literatures such as "New Edition Polymer Dictionary" (The Society of Polymer Science, edited by polymer dictionary editing committee, published by Asakura Shoten) and the "Graduate School Polymer Chemistry (KS Chemical specialized book)" (edited by NOSE Takuhei et al., published by Kodansha) can be referred to.

In the production method according to the present aspect, the first star-shaped polymer and the second star-shaped polymer (the third, fourth, . . . star-shaped polymer used if necessary) contain a water soluble unsaturated monomer having a dissociable group as a main component of the repeating unit of each branched chain.

Here, as the specific modes and preferred embodiments of the "water soluble unsaturated monomer having a dissociable group" serving as the main component of the repeating unit of the branched chain of the star-shaped polymer and the modes and the like of a water soluble unsaturated monomer which can be used other than the "water soluble unsaturated monomer having a dissociable group", the same modes that described above in the section for the "(2-1) Configuration of water-absorbing resin" may be employed, and the detailed description thereon is thus omitted here. That is, in the production method according to the present aspect as well, it is preferable that 90 mol % or more of the repeating unit of each branched chain of the star-shaped polymer be a repeating unit derived from acrylic acid (salt).

In addition, in the present invention, the number of branched chains with respect to one core of the star-shaped polymer is not particularly limited, but it is preferably from 3 to 100, more preferably from 3 to 10, and particularly preferably 4. When a plurality of star-shaped polymers used in the reaction step all have four branched chains, each star-shaped polymer has a tetrahedral structure and as a result, the internal crosslinked structure thus obtained is a diamond structure. It can be said that a water-absorbing resin having such a diamond structure as the internal crosslinked structure is a particularly preferred one since it has higher network uniformity and a high swollen gel elastic modulus. That is, the star-shaped polymer preferably has a structure in which a polymer containing the water soluble unsaturated monomer having a dissociable group as a main component of the repeating unit is bonded to the core with four arms as a branched chain.

Each star-shaped polymer has a reactive functional group at the terminal of each branched chain. Moreover, it is required that the reactive functional group present at the terminal of each branched chain of each star-shaped polymer is capable of forming a chemical bond with a reactive functional group present at the terminal of each branched chain of at least another star-shaped polymer by reacting with each other. For example, when only two kinds of star-shaped polymer are used as exemplified in the section for Examples described later, it is required that the reactive functional group present at the terminal of each branched chain of the second star-shaped polymer (also referred to as the "second reactive functional group") is capable of forming a chemical bond with a reactive functional group present at the terminal of each branched chain of the first star-shaped polymer (also referred to as the "first reactive functional group") by reacting with each other. Incidentally, the reactive functional groups present at the terminal of the respective three or more (preferably four) branched chains constituting one star-shaped polymer may be the same as or different from one another, but they are preferably the same as one another.

The combination of the reactive functional groups present at the terminal of each branched chain of each star-shaped polymer typified by the combination of the first reactive functional group and the second reactive functional group is not particularly limited, and an arbitrary combination of reactive functional groups can be used as long as the reactive functional groups do not react with the moieties other than the reactive functional group such as the core and branched chain which constitute the star-shaped polymer when the reactive functional groups react with each other in the reaction step. Specific examples of such a combination of the reactive functional groups (first reactive functional group; second reactive functional group) may include (azido group; alkynyl group), (thiol group; alkenyl group), (hydrosilyl group; alkenyl group), (conjugated diene group; alkenyl group), and (amino group; NHS-activated ester group). Among them, a combination of (azido group; alkynyl group) is preferably used from the viewpoint of the functional group selectivity of reaction.

The method for obtaining a star-shaped polymer is not particularly limited, and the knowledge known in the prior art can be appropriately referred to. As an example, in order to obtain a star-shaped polymer, an atom or an atomic group constituting the core is first prepared. As the core, an arbitrary polyfunctional compound or a compound obtained by modifying this can be used. Examples of the polyfunctional compound may include a polyol such as pentaerythritol, trimethylol propane, arabitol, or mannitol; and a polyamine such as triethylenetetramine. The valence (number of molecular chain) of the star-shaped polymer obtained is determined by the valence of the atom or atomic group as the core prepared at this time. For example, when pentaerythritol, which is a tetrahydric alcohol, is used as the core, a (tetravalent) star-shaped polymer having four branched chains is obtained. In addition, examples of the operation for modifying a polyfunctional compound may include an operation in which an acyl compound is reacted with the functional group (hydroxyl (—OH) group in this example) in a polyfunctional compound for the esterification thereof as described later in the section for the "Synthesis of star-shaped core with four arms" in Examples. When the polyfunctional compound is modified in advance in this manner, it is possible for the subsequently followed synthesis reaction of the main chain to advantageously proceed.

Subsequently, the synthesis reaction (polymerization reaction) of the main chain of the branched chain constituting the star-shaped polymer is conducted by using the core prepared above. With regard to the polymerization reaction, techniques known in the prior art (chain polymerization such as radical polymerization, cationic polymerization, anionic polymerization, or living radical polymerization, living cationic polymerization, and living anionic polymerization; and condensation polymerization) can be used. Among them, chain polymerization is preferable and radical polymerization or living radical polymerization is particularly preferable.

At this time, in the synthesis reaction (polymerization reaction) of the main chain of the branched chain constituting the star-shaped polymer, the reaction is conducted by using a monomer component containing a water soluble unsaturated monomer having a dissociable group as the main component. In this case, it is preferable to protect the dissociable group of the water soluble unsaturated monomer having a dissociable group contained in the monomer component used in this reaction with a protecting group. For example, when conducting the synthesis reaction (polymerization reaction) of the main chain of the branched chain by using a monomer component containing acrylic acid (salt) having a carboxyl group as a dissociable group, it is preferable to protect the carboxyl group, which is the dissociable group, with a protecting group such as a tertiary butyl ester group, a methyl ester group, or an amide group. It is preferable to protect the dissociable group with a protecting group in this manner and to carry out the de-protection step after the reaction step for reacting a plurality of star-shaped polymers with one another are carried out since the reaction of the star-shaped polymers in the reaction step is not affected by the dissociable group. Incidentally, in the production method according to the present aspect, the "star-shaped polymer" used as a reaction raw material contains the "water soluble unsaturated monomer having a dissociable group" as a main component of the repeating unit of each branched chain. Here, in this specification, the concept of the "water soluble unsaturated monomer having a dissociable group" includes a monomer in which the dissociable group is protected with a protecting group as described above.

It is preferable to carry out a step for introducing a reactive functional group (first reactive functional group) to the terminal of each branched chain of each star-shaped polymer after the synthesis reaction (polymerization reaction) of the main chain of the branched chain is conducted in this manner. The specific method for carrying out this step is also not particularly limited, and the knowledge known in the prior art can be appropriately referred to depending on the kind of the reactive functional group to be introduced. For example, in a case when a halogen atom such as a chlorine atom, a bromine atom, or an iodine atom is bonded to the terminal of each branched chain at the endpoint of the synthesis reaction (polymerization reaction) of the main chain of the branched chain, the halogen atom can be substituted with an azido group by allowing sodium azide ($NaN_3$) to act as a nucleophilic agent and thus a star-shaped polymer having an azido group introduced into the terminal of each branched chain can be obtained. Here, the introduction of a reactive functional group into the terminal of each branched chain may be conducted by a reaction consisting of two or more stages. For example, it is possible to obtain a star-shaped polymer having an alkynyl group introduced into the terminal of each branched chain by conducting a series of reactions as described in the section for the "Synthesis of dialkyne", "Synthesis of star-shaped polymer with four arms (1-Si alkyne)", and "Synthesis of star-shaped polymer with four arms (1-H alkyne)" of Examples described later.

The weight average molecular weight (Mw) of the star-shaped polymer obtained in this manner is not particularly limited, but it is preferably 1,000 or more, more preferably 2,000 or more, even more preferably 5,000 or more, and particularly preferably 10,000 or more in order to obtain a water-absorbing resin having a sufficiently great equilibrium swelling capacity. Incidentally, the method for measuring the weight average molecular weight (Mw) of the star-shaped polymer will be described in detail in the section for Examples later.

In the reaction step, the reaction conditions (reaction temperature, reaction time, reaction solvent, and equivalent relationship among star-shaped polymers) at the time of reacting the first star-shaped polymer and the second star-shaped polymer (and further the third, fourth, . . . star-shaped polymer) can be appropriately set by those skilled in the art while referring to the knowledge known in the prior art depending on the kind of the reactive functional groups used and the kind of the reaction based on the kind of the reactive functional groups. For example, in the case of using an azido group as the first reactive functional group and an alkynyl group as the second reactive functional group, it is possible to form a chemical bond having a 1,2,3-triazole structure between the branched chain of the first star-shaped polymer and the branched chain of the second star-shaped polymer by conducting a cycloaddition reaction in the presence of a copper catalyst. In this case, the range of the reaction temperature is preferably from 0 to 100° C. and the range of the reaction time is preferably from 1 minute to 96 hours. In addition, examples of the reaction solvent may include an organic solvent such as an ether such as diethyl ether, an ester such as ethyl acetate, a halogenated hydrocarbon such as dichloromethane, a nitrile such as acetonitrile, a ketone such as acetone, or a sulfoxide such as dimethyl sulfoxide, and a water-based solvent such as water. With regard to the equivalent relationship between the reactants, the range of the second reactive functional group per 1 mol equivalent of the first reactive functional group is preferably from 0.80 to 1.20 mol equivalent and most preferably 1.00 mol equivalent.

Incidentally, as described above, it is preferable to conduct the reaction step for the production method according to the present aspect in a state in which the dissociable group of the water soluble unsaturated monomer having a dissociable group constituting the branched chain of the first star-shaped polymer and the second star-shaped polymer (and the third, fourth, . . . star-shaped polymer) is protected with a protecting group. In this case, it is common to include further the step for de-protecting the dissociable group after the reaction step is completed. For example, when a tertiary butyl group is used as the protecting group of a carboxyl group as the dissociable group, the carboxyl group of the dissociable group is released by conducting the de-protection reaction using trifluoroacetic acid, and thus it is possible to obtain a water-absorbing resin which contains a water soluble unsaturated monomer having a dissociable group (for example, acrylic acid) as a main component of the repeating unit of the main chain and has an internal cross-linked structure.

It is possible to obtain finally a water-absorbing resin having a desired rate of neutralization by subjecting the water-absorbing resin thus obtained to the neutralization step using a base such as sodium (hydrogen) carbonate or sodium hydroxide.

(3-3) Other Steps

In the production method according to the present aspect, for example, a water-absorbing resin in a state of a water-swollen gel may be recovered as the end product when the neutralization step described above is completed. In some cases, the water-absorbing resin may be subjected to subsequent processes such as drying, crushing, classification, and surface crosslinking in the same manner as the water-absorbing resin known in the prior art. Hereinafter, the respective steps will be briefly described.

(Drying)

When the water-absorbing resin obtained in the reaction step (and the neutralization step) is a water-swollen gel, the water-absorbing resin may be recovered as a dry polymer by being dried and usually crushed before and/or after drying. Incidentally, in the present specification, the term "drying" is a step for obtaining a dry polymer by drying a water-swollen gel until to have a desired moisture content. The moisture content is measured in conformity to the EDANA Method (ERT430.2-02) by setting the sample amount to 1.0 g, the drying temperature to 180° C., and the drying time to 4 hours, and the moisture content is preferably 20 wt % or less, more preferably from 1 to 15 wt %, even more preferably from 2 to 10% by weight, and particularly preferably from 3 to 8 wt %.

The method for drying the water-swollen gel is not particularly limited, and examples thereof may include drying by heating, hot air drying, vacuum drying, fluidized bed drying, infrared drying, microwave drying, drying by a drum dryer, drying by azeotropic dehydration with a hydrophobic organic solvent, and a high humidity drying utilizing high temperature steam. Among them, from the viewpoint of the drying efficiency, hot air drying is preferable and band drying for conducting hot air drying on a ventilation belt is more preferable.

From the viewpoint of the color tone of the water-absorbing resin and the drying efficiency, the drying temperature (temperature of hot air) in the hot air drying is preferably from 120 to 250° C. and more preferably from 150 to 200° C. Incidentally, the drying conditions such as the wind velocity of the hot air and the drying time other than the drying temperature may be appropriately set depending on the moisture content and total weight of the particulate hydrogel to be subjected to the drying and the intended solids content of the resin, and when band drying is conducted, the conditions described in WO 2006/100300 A, WO 2011/025012 A, WO 2011/025013 A, WO 2011/111657 A, and the like are appropriately applied.

(Crushing and Classification)

It is preferable that the dry polymer obtained in the drying step be crushed by a crusher. The crusher is not particularly limited, but for example, a roll type crusher such as a roll mill, a hammer type mill such as a hammer mill, an impact type mill, a cutter mill, a turbo grinder, a ball mill, a flash mill and the like are used. Among these, a roll mill is preferable in order to control the particle size distribution. In order to control the particle size distribution, the dry polymer may be crushed two or more times in succession and the dry polymer is preferably crushed three or more times. In the case of crushing two or more times, the crusher used for each time may be the same as or different from one another. It is also possible to use different kinds of crushers in combination.

It is preferable to classify the water-absorbing resin thus crushed by using a sieve with a specific aperture in order to control the particle size distribution of the water-absorbing resin thus crushed to a specific one. The classifier is not particularly limited, but for example, a vibration sieve (unbalanced weight driving type, resonance type, vibrating motor type, electromagnetic type, circular vibrating type, and the like), an in-plane motion sieve (horizontal motion type, horizontal circle-linear motion type, three-dimensional circular motion type, and the like), a mobile network type sieve, a forced stirring type sieve, a net surface vibrating type sieve, a wind power sieve, a sound wave sieve or the like are used, and preferably a vibration sieve or an in-plane motion sieve are used. The aperture of the sieve is in a range of preferably from 1,000 µm to 300 µm, more preferably 900 µm to 400 µm, and most preferably from 710 µm to 450 µm. When the aperture of the sieve is out of these ranges, there is a possibility that the intended particle size distribution is not obtained.

In order to control the particle size distribution of the water-absorbing resin of the present invention to a specific one, apart or the whole of the particles having a particle diameter less than a specific particle diameter may be removed by further classifying the water-absorbing resin. The classifier in this step is not particularly limited, but for example, those exemplified above are preferably used, and a pulverization type classifier (centrifugal force type, inertial force type, and the like) or the like are used in addition to those exemplified above. In this step, a part or the whole of the particles having a particle diameter preferably less than 200 µm, more preferably less than 150 µm, and most preferably less than 106 µm are removed.

The shape of the water-absorbing resin obtained by the respective steps described above is generally a single particle shape such as an irregular crushed shape, a spherical shape, a fibrous shape, a rod shape, a substantially spherical shape, or a flat shape or a granulated particle shape formed as these are joined. It is preferable that the shape be an irregular crushed shape or a granulated particle shape since the water-absorbing resin can be easily immobilized, for example, when being used in a water-absorbing material. In addition, as the proportion of the particles having an irregular crushed shape or granulated particle shape in the water-absorbing resin is preferably 50% or more, more preferably 70% or more, and even more preferably 90% or more in the number ratio of the total number thereof. Incidentally, the shape can be observed by a visual inspection (including a visual inspection of the enlarged image by a microscope or the like). It is not necessary to measure the number ratio by observing all of the particles, and the number ratio thereof can be determined by sampling 10 sets of about 100 particles while changing the sampling location and measuring the arithmetic mean value of the respective measurement results, namely, measuring about 1,000 particles in total.

(Surface Crosslinking)

It is preferable that the vicinity of the surface of the water-absorbing resin according to the present invention, be surface-crosslinked with an organic surface crosslinking agent and/or a water soluble inorganic surface crosslinking agent that are a surface crosslinking agent. That is, it is preferable that the method for producing a water-absorbing resin of the present invention include a step for surface-crosslinking the water-absorbing resin after drying.

When the vicinity of the surface of the water-absorbing resin is crosslinked with a surface crosslinking agent, it is possible to decrease the amount of liquid returned occurring when a pressure is applied to the swollen water-absorbing resin. Hence, it is possible to increase AAP and SFC. As a result, when the water-absorbing resin is used in a water-absorbing material, it is possible to obtain a water-absorbing material having a small amount of liquid returned (commonly called Re-Wet) when a pressure is applied thereto and an excellent uptake rate of a liquid into the water-absorbing material.

Examples of the surface crosslinking agent that can be used in the surface crosslinking treatment may include an organic surface crosslinking agent and/or a water soluble inorganic surface crosslinking agent that have two or more functional groups capable of reacting with the functional group, particularly a carboxyl group of the water-absorbing resin. Preferably, a water soluble organic surface crosslinking agent can be used.

Examples thereof may include a polyhydric alcohol such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, an oxyethylene-oxypropylene block copolymer, pentaerythritol, and sorbitol; an epoxy compound such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; a polyvalent amine compound such as ethylenediamine, diethylenetriamine, triethylenetetramine, tetraethylenepentamine, pentaethylenehexamine, and polyethyleneimine and any inorganic salt or organic salt (for example, azetidinium salt and the like) thereof; a polyvalent isocyanate compound such as 2,4-tolylene diisocyanate and hexamethylene diisocyanate; a polyvalent oxazoline compound such as 1,2-ethylenebisoxazoline; a carbonic acid derivative such as urea, thiourea, guanidine, dicyandiamide, or 2-oxazolidinone; an alkylene carbonate compound such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, or 1,3-dioxopan-2-one; a haloepoxy compound such as epichlorohydrin, epibromohydrin, or α-methylepichlorohydrin and a polyvalent amine adduct thereof (for example, Kymene: registered trademark manufactured by SOLENIS); an silane coupling agent such as γ-glycidoxypropyltrimethoxysilane or γ-aminopropyltriethoxysilane; and an oxetane compound such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, 3-butyl-3-oxetaneethanol, 3-chloromethyl-3-methyloxetane, 3-chloromethyl-3-ethyloxetane, or a polyvalent oxetane compound.

These surface crosslinking agents may be used singly, or two or more kinds thereof may be used concurrently. Among them, a polyhydric alcohol is preferable from the viewpoint of having high safety and of being able to improve the hydrophilicity of the water-absorbing resin surface.

The amount of the surface crosslinking agent used is preferably 0.001 parts by mass or more and 5 parts by mass or less per 100 parts by mass of the solids content in the water-absorbing resin.

When the surface crosslinking agent is mixed with the water-absorbing resin, water may be used. The amount of water used is in a range of preferably more than 0.5 part by mass and 10 parts by mass or less and more preferably 1 part by mass or more and 5 parts by mass or less per 100 parts by mass of the solids content in the water-absorbing resin.

When the surface crosslinking agent or an aqueous solution thereof is mixed with the water-absorbing resin, a hydrophilic organic solvent or a third substance may be used as a mixing aid. In the case of using a hydrophilic organic solvent, examples thereof may include a lower alcohol such as methyl alcohol, ethyl alcohol, n-propyl alcohol, isopropyl alcohol, n-butyl alcohol, isobutyl alcohol, or t-butyl alcohol; a ketone such as acetone; an ether such as dioxane, tetrahydrofuran, or methoxy (poly)ethylene glycol; an amide such as ε-caprolactam or N, N-dimethylformamide; a sulfoxide such as dimethyl sulfoxide; and a polyhydric alcohol such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerine, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, anoxyethylene-oxypropylene block copolymer, pentaerythritol, or sorbitol.

The amount of the hydrophilic organic solvent used depends on the kind, particle diameter, moisture content, and the like of the water-absorbing resin, but it is preferably 10 parts by mass or less and more preferably in a range of 0 part by mass or more and 5 parts by mass or less per 100 parts by mass of the solids content in the water-absorbing resin.

Further, as the third substance, an inorganic acid, an organic acid, a polyamino acid, or the like disclosed in EP0668080 may be allowed to exist. These mixing aids may act as a surface crosslinking agent, but those that do not decrease the water absorbing performance of the water-absorbing resin after the surface crosslinking are preferable. The water-absorbing resin according to the present invention is preferably crosslinked by being mixed with a surface crosslinking agent not containing a hydrophilic organic solvent having a boiling point of 100° C. or lower and then being heated. When the water-absorbing resin contains a hydrophilic organic solvent having a boiling point of 100° C. or lower, there is a risk that the presence state of the surface crosslinking agent on the water-absorbing resin surface may change by vaporization of the hydrophilic organic solvent and the physical properties such as SFC (Saline Flow Conductivity) may not be sufficiently satisfied.

In order to mix the water-absorbing resin with the surface crosslinking agent more uniformly, it is preferable that a water soluble inorganic salt (preferably, a persulfate) be allowed to coexist when the water-absorbing resin is mixed with the surface crosslinking agent. The amount of the water soluble inorganic salt used depends on the kind, particle diameter, and the like of the water-absorbing resin, but it is preferably in a range of 0.01 part by mass or more and 1 part by mass or less and more preferably in a range of 0.05 part by mass or more and 0.5 part by mass or less per 100 parts by mass of the solids content in the water-absorbing resin. That is, the water-absorbing resin according to the present invention is preferably crosslinked by being mixed with an organic surface crosslinking agent and/or a water soluble inorganic surface crosslinking agent which contain a water soluble inorganic salt, preferably a persulfate at 0.01 mass % or more and 1.0 mass % or less per the water-absorbing resin, and then being heated.

The mixing method for mixing the water-absorbing resin with a surface crosslinking agent is not particularly limited, but examples thereof may include a method in which the water-absorbing resin is immersed in a hydrophilic organic solvent and mixed with a surface crosslinking agent dissolved in water and/or a hydrophilic organic solvent if necessary and a method in which the water-absorbing resin is mixed with a surface crosslinking agent by directly spraying or adding dropwise the surface crosslinking agent dissolved in water and/or a hydrophilic organic solvent to the water-absorbing resin.

After the water-absorbing resin is mixed with a surface crosslinking agent, it is preferable to usually perform the crosslinking reaction by conducting a heat treatment. The temperature for the heat treatment (temperature of heating medium) depends on the used surface crosslinking agent, but it is preferably 40° C. or higher and 250° C. or lower and more preferably 150° C. or higher and 250° C. or lower. In a case when the temperature for the heat treatment is lower than 40° C., there is a risk that the absorption properties such as AAP (Absorption Against Pressure) and SFC (Saline Flow Conductivity) may not be sufficiently improved. In a case when the temperature for the heat treatment exceeds 250° C., attention is required since deterioration of the water-absorbing resin may be caused and various kinds of physical properties may decrease in some cases. The time for the heat treatment is preferably one minute or longer and two hours or shorter and more preferably five minutes or longer and one hour or shorter.

Further, it is preferable that the surface crosslinking be conducted in the presence of an α-hydroxycarboxylic acid (salt). By doing so, the effect of preventing coloration of the water-absorbing resin is obtained.

(Additive Such as Polyvalent Metal Salt)

In the method for producing a water-absorbing resin according to the present invention, it is preferable to add a polyvalent metal salt to the water-absorbing resin (to add preferably to the particle surface) particularly at the time of surface crosslinking or after surface crosslinking. The amount of the polyvalent metal salt added is preferably 0.001 mass % or more and 5 mass % or less and more preferably 0.01 mass % or more and 1 mass % or less per the water-absorbing resin.

It is possible to improve SFC without significantly decreasing AAP of the water-absorbing resin by adding a polyvalent metal salt (preferably a trivalent water soluble polyvalent metal salt) to the water-absorbing resin according to the present invention.

Specific examples of the polyvalent metal salt which can be used in the present invention may include a sulfate, a nitrate, a carbonate, a phosphate, an organic acid salt, and a halide (chloride or the like) of a metal selected from Zn, Be, Mg, Ca, Sr, Al, Fe, Mn, Ti, Zr, Ce, Ru, Y, or Cr, and specific examples thereof may further include polyvalent metal salts described in JP 2005-11317 A or the like.

Further, it is most preferable to use a trivalent water soluble metal salt among the polyvalent metal salts. Specific examples of the trivalent water soluble polyvalent metal salt may include aluminum chloride, polyaluminum chloride, aluminum sulfate, aluminum nitrate, potassium aluminum sulfate, sodium aluminum sulfate, potassium alum, ammonium alum, sodium alum, sodium aluminate, iron(III) chloride, cerium(III) chloride, ruthenium(III) chloride, yttrium (III) chloride, chromium(III) chloride and the like.

Moreover, from the viewpoint of solubility of the absorbed liquid such as urine, it is preferable to use these salts having crystal water. Particularly preferred one is an aluminum compound, and among them, aluminum chloride, polyaluminum chloride, aluminum sulfate, aluminum nitrate, potassium aluminum bissulfate, sodium aluminum bissulfate, potassiumalum, ammonium alum, sodium alum, and sodium aluminate are preferable, aluminum sulfate is particularly preferable, and an aqueous aluminum sulfate solution (preferably a solution having an aluminum sulfate concentration to be 90% or more of the saturated concentration thereof) can be most suitably used. These may be used singly, or two or more kinds thereof may be used concurrently.

Further, in the present invention, from the viewpoint of the color tone (prevention of coloration), prevention of deterioration, and the like of the obtained water-absorbing resin, it is preferable to add a chelating agent. As the chelating agent, specifically, the compounds and the used amount thereof disclosed in the "[2] Chelating agent" of WO 2011/040530 A are applied to the present invention.

Furthermore, in the present invention, additives other than the additives described above may be added in order to impart various functions to the water-absorbing resin. Specific examples of the additives may include a surfactant, a compound having a phosphorus atom, an oxidizing agent, an organic reducing agent, water insoluble inorganic fine particles, organic powders such as metal soaps, a deodorant, an antimicrobial agent, pulp, and a thermoplastic fiber. Incidentally, the compounds disclosed in WO 2005/075070 A and the compounds disclosed in the "[5] Water insoluble inorganic fine particles" of WO 2011/040530 A are applied to the present invention as the surfactant and the water insoluble inorganic fine particles, respectively. The amount of the additive used (added amount) is not particularly limited since it is appropriately determined depending on the application thereof, but it is preferably from 0.001 mass % or more and 3 wt % or less and more preferably 0.01 mass % or more and 1 wt % or less per 100 parts by weight of the water-absorbing resin powder. In addition, the additive can be added in a separate step from the above step.

CRC of the water-absorbing resin according to the present invention is usually 5 (g/g) or more, preferably 15 (g/g) or more, and even more preferably 25 (g/g) or more. The upper limit value of CRC is not particularly limited, but it is preferably 70 (g/g) or less, more preferably 50 (g/g) or less, and even more preferably 40 (g/g) or less. When CRC is less than 5 (g/g), the absorption amount is too small in the case of using the water-absorbing resin in a water-absorbing material and the water-absorbing resin is thus not suitable for use in hygienic materials such as diapers. Further, when CRC is greater than 70 (g/g), there is a risk that a water-absorbing resin having an excellent uptake rate of a liquid into the water-absorbing material cannot be obtained in the case of using the water-absorbing resin in a water-absorbing material.

AAP of the water-absorbing resin according to the present invention is preferably 20 (g/g) or more, more preferably 22 (g/g) or more, even more preferably 23 (g/g) or more, and particularly preferably 24 (g/g) or more. The upper limit value of AAP is not particularly limited, but it is preferably 30 (g/g) or less. When AAP is less than 20 (g/g), there is a risk that a water-absorbing resin having a small amount of liquid returned (commonly called Re-Wet) at the time when a pressure is applied to the water-absorbing resin cannot be obtained in the case of using the water-absorbing resin in a water-absorbing material.

SFC (Saline Flow Conductivity) of the water-absorbing resin of the present invention is preferably 50 ($\times 10^{-7} \cdot cm^3 \cdot s \cdot g^{-1}$) or more, more preferably 60 ($\times 10^{-7} \cdot cm^3 \cdot s \cdot g^{-1}$) or more, even more preferably 70 ($\times 10^{-7} \cdot cm^3 \cdot s \cdot g^{-1}$) or more, and particularly preferably 80 ($\times 10^{-7} \cdot cm^3 \cdot s \cdot g^{-1}$) or more. The upper limit value thereof is not particularly limited, but it is preferably 3,000 ($\times 10^{-7} \cdot cm^3 \cdot s \cdot g^{-1}$) or less and more preferably 2,000 ($\times 10^{-7} \cdot cm^3 \cdot s \cdot g^{-1}$) or less. When SFC is less than 50 ($\times 10^{-7} \cdot cm^3 \cdot s \cdot g^{-1}$), liquid permeability of body fluids such as urine, blood or the like through the water-absorbing resin is low and the water-absorbing resin is thus not suitable as an absorbent material of hygiene products such as disposable diapers. Further, when SPC exceeds 3,000 ($\times 10^{-7} \cdot cm^3 \cdot s \cdot g^{-1}$), there is a risk that body fluids such as urine, blood or the like leaks without being sufficiently absorbed and the water-absorbing resin is thus not suitable as an absorbent material of hygiene products such as disposable diapers. Incidentally, SFC can be controlled by the particle size, a surface crosslinking agent, a polyvalent metal salt, a cationic polymer, and the like.

In the water-absorbing resin according to the present invention, the amount of water soluble contents (water soluble component) is preferably from 0 to 35 mass %, more preferably from 0 to 25 mass %, and even more preferably from 0 to 15 mass %. When the amount of water soluble contents (water soluble component) exceeds 35 mass %, there is a case in which the water-absorbing resin becomes one that has a weak gel strength and is inferior in liquid permeability. In addition, there is a risk that a water-absorbing resin having a small amount of liquid returned (commonly called Re-Wet) when a pressure is applied to the water-absorbing material cannot be obtained in the case of using the water-absorbing resin in a water-absorbing material.

The water-absorbing resin according to the present invention preferably has a mass average particle diameter (D50) of from 200 to 600 µm. The mass average particle diameter is more preferably from 300 to 500 µm. When the mass average particle diameter (D50) of the water-absorbing resin is out of the range of from 200 to 600 µm, it is possible that the liquid permeability and diffusibility significantly decrease or the absorption speed greatly decreases. When such a water-absorbing resin is used in diapers, there is a risk that leakage of the liquid is caused, for example.

In the water-absorbing resin according to the present invention, a logarithmic standard deviation (σζ) of particle size distribution is preferably from 0.20 to 0.50 and even more preferably from 0.30 to 0.40. When the logarithmic standard deviation of particle size distribution is out of the above range, there is a risk that the liquid permeability decreases and the uptake rate of a liquid into the water-absorbing material significantly deteriorates.

In the water-absorbing resin according to the present invention, it is preferable that the proportion of the particles having a size so as to pass through a sieve having an aperture of 150 µm and the proportion of the particles having a size of 850 µm or more be respectively from 0 to 5 mass %, and it is more preferable that the proportions are respectively from 0 to 3 mass %. By using a water-absorbing resin containing particles having a size in a range of less than 150 µm in a small amount is used, it is possible to suppress the amount of dust in the obtained water-absorbing resin. Hence, it is possible to prevent problems on safety and health caused by scattering of fine particles contained in the water-absorbing resin at the time of production of the water-absorbing resin and to suppress a decrease in physical properties of the obtained water-absorbing resin. Incidentally, when the proportion exceeds 5 mass %, dust is likely to be generated at the time of production of the water-absorbing resin, and thus a problem on safety and health may occur or there is a risk that a decrease in physical properties of the water-absorbing material is caused.

EXAMPLES

Hereinafter, the embodiments of the present invention will be described in detail in accordance with Examples, but the present invention is not construed by being limited to the Examples. Moreover, the physical properties described in the claims and the Examples of this application were determined according to the following measuring methods. Incidentally, unless otherwise stated, the respective steps in the respective Examples were carried out at substantially atmospheric pressure (±5% of the atmospheric pressure, even more preferably within 1%), and the same step was carried out without changing the pressure by pressurization or pressure reduction intentionally.

[Method for Measuring Physical Properties]

In a polypropylene container, the water-absorbing resin (in an amount in which 1.6 to 20 g of swollen gel is obtained) was immersed in an excess amount (weight to be 1,000 times or more of the water-absorbing resin) of a 0.9 wt % aqueous sodium chloride solution (temperature: 21 to 25° C.), and the container was left to stand still for 48 hours. Thereafter, the aqueous solution in the polypropylene container was removed, and an excess amount of a 0.9 wt % aqueous sodium chloride solution was added into the polypropylene container again, the container was left to stand still for 48 hours. Thereafter, the aqueous solution in the polypropylene container was removed, and an excess amount of a 0.9 wt % aqueous sodium chloride solution was added into the polypropylene container again, the container was left to stand still for 48 hours, thereby obtaining a dispersion of the gel in an equilibrium swollen state (hereinafter, equilibrium swollen gel).

The equilibrium swollen gel thus obtained was weighed in a range of from 1.6 to 2.4 g (mass W1) until a 0.1 mg unit, and the equilibrium swelling capacity (the ratio (g/g) of the amount (g) of the 0.9 wt % aqueous sodium chloride solution absorbed by the water-absorbing resin to the solids content in the water-absorbing resin W (g)) represented by the following formula was determined from the mass (W1) of the equilibrium swollen gel and the polymer solids content W of the equilibrium swollen gel.

Equilibrium swelling capacity with respect to 0.9 wt % saline solution (g/g)=W1/W−1

Note that the mass (W1) of the equilibrium swollen gel and the polymer solids content W are determined below.

(Method for Measuring Mass W1 of Equilibrium Swollen Gel)

In a resin cylinder for measuring AAP described in ERT442.2-02 (inner diameter: 6 cm and height: 5 cm) which had a wire mesh with an aperture of 36 μm (corresponding to 400 mesh) at the bottom, the entire amount of the dispersion of equilibrium swollen gel obtained above was put and then subjected to draining by natural filtration for 5 minutes. After the filtration, the gel was further put in the cylinder with a spatula into a flat shape so as to cover the entire cylinder bottom without compressing when the gel was a particulate shape. Alternatively, when the gel was a massive gel, the gel was further put in the cylinder so as to have the maximum contact base area of the massive gel with respect to the cylinder bottom. Thereafter, for further draining, this cylinder was placed on five sheets of filter paper (Advantec No. 2, diameter: 150 mm) superimposed and left to stand still for 5 minutes in an environment at room temperature of from 15 to 30° C. and a humidity of from 30 to 90%. Thereafter, this cylinder was placed on five sheets of filter paper (Advantec No. 2, diameter: 150 mm) newly superimposed and left to stand still for 5 minutes in an environment at room temperature of from 15 to 30° C. and a humidity of from 30 to 90%, and the gel was taken from the drained gel and weighed by a predetermined weight (mass W1).

(Method for Measuring Polymer Solids Content W in Equilibrium Swollen Gel)

The polymer solids content in the equilibrium swollen gel (mass W1) was determined by the amount lost from drying. Here, NaCl solids content in the gel was first removed by the following method at that time. That is, the gel (mass W1) thus weighed was transferred to a polypropylene container having a capacity of 250 ml (manufactured by TGK), and immersed in 200 ml of pure water (temperature: 21 to 25° C.), the lid was put on the container, and the container was left to stand still for 48 hours. Thereafter, the liquid in the polypropylene container was removed, 200 ml of pure water (temperature: 21 to 25° C.) was added into the container again, the lid was put on the container, and the container was left to stand still for 48 hours. Thereafter, the liquid in the polypropylene container was removed, 200 ml of pure water (temperature: 21 to 25° C.) added into the container again, the lid was put on the container, and the container was left to stand still for 48 hours.

The pure water-swollen gel obtained by removing NaCl therefrom was placed on an aluminum cup (weight W0) having a diameter of the bottom surface of about 5 cm. In a case when the length of the pure water-swollen gel thus obtained was greater than 3 mm, the gel was chopped with scissors until to have a length of about 3 mm. This aluminum cup was left to stand still for 4 hours in a windless dryer (ADVANTEC DRV320DA) at 180° C. to dry the gel. After drying, the sum (W2) of the mass of the aluminum cup and the mass (solids content) of the crosslinked polymer was measured, and the polymer solids content W (=W2−W0) in the equilibrium swollen gel (W1) was determined.

<Swollen Gel Elastic Modulus>

(Sample Preparation)

The gel which had reached the equilibrium swollen state in a 0.9 wt % aqueous sodium chloride solution was transferred to a stainless-steel vat (20 cm×12.5 cm×7 cm). The gel was cut into a cylindrical shape having a diameter of 25 mm by using a steel punch (POSK25 higher belt punch 25 mm manufactured by TRUSCO NAKAYAMA CORPORATION). The elastic modulus of this gel was measured by a shear test under the following conditions.

(Conditions for Measuring Elastic Modulus)

Apparatus for measurement: MCR 301 (manufactured by Anton Paar GmbH)

Jig: Aluminum plate having diameter of 25 mm

Distortion: 0.01%

Frequency: 1 Hz

Measuring method: First, a shear was applied to the gel under a load of 0.34 N under the above conditions, and the storage elastic modulus was measured every 10 seconds for 5 minutes. The average value of the storage elastic modulus in from 120 seconds to 300 seconds after the starting of the measurement was adopted as the elastic modulus ($G_0$) under a load of 0.34 N. Thereafter, the load applied to the gel was gradually increased stepwise by 0.68 N (namely, the load was (0.34+0.68×n) N (n=1, 2, 3, . . . m−1, m, m+1, . . . )), the elastic modulus ($G_n$) under each load was measured. $G_m$ was adopted as the elastic modulus of the gel at the time point at which the deviation between the measured value ($G_m$) of the elastic modulus under a load of (0.34+0.68× m) N and the measured value ($G_{m+1}$) of the elastic modulus under a load immediately before, and the deviation between the measured value ($G_m$) of the elastic modulus under a load of (0.34+0.68× m) N and the measured value ($G_{m+1}$) of the elastic modulus under a load immediately after were both within 5%.

<Weight Average Molecular Weight after Hydrolysis Treatment>

(Sample Preparation)

The gel which had reached the equilibrium swollen state in a 0.9 wt % aqueous sodium chloride solution was weighed by (50× equilibrium swelling capacity with respect to physiological saline solution) mg and put in a polypropylene container having a capacity of 120 ml (manufactured by TGK). 10 g of a 0.1 mol/l aqueous sodium hydroxide solution was added into the container, the lid was put on the container, and the container was left to stand still for three weeks in a windless dryer (ADVANTEC DRV320DA) at 80° C. After three weeks, the gel was hydrolyzed to be in a solution state.

The solution thus obtained was diluted 4-fold with the following eluent and allowed to pass through a filter (manufactured by GL Sciences Inc., GL Chromatodisc, water-based 25 A, pore size: 0.2 μm). The GPC measurement of this solution was conducted under the following conditions.

(Conditions for GPC Measurement)

The measurement was conducted by using the TDA302 (registered trademark) manufactured by Malvern Instruments Ltd. The apparatus configuration included a size exclusion chromatograph, a refractive index detector, a light scattering detector, and a capillary viscometer mounted on the apparatus. The apparatus and the conditions for the measurement were as follows.

Pump and auto sampler: GPCmax manufactured by Malvern Instruments Ltd.

Guard column: OHpak SB-G (manufactured by SHOWA DENKO K. K.)

Column: two pieces of OHpak SB-806MHQ (manufactured by SHOWA DENKO K.K.) were used by being connected in series Detector: TDA302 (the temperature in the system was kept at 30° C.) manufactured by Malvern Instruments Ltd.

Eluent: aqueous solution (pH: 6.35 to 6.38) of 60 mM sodium dihydrogen phosphate dihydrate, 20 mM disodium hydrogen phosphate dodecahydrate, and 400 ppm sodium azide Flow rate: 0.5 ml/min Injection volume: 100 μl As the pure water used in this measurement, water from which impurities were sufficiently removed was used. Further, the measurement was conducted in a state in which the base line of the detector was stabilized by running a sufficient amount of the solvent through the apparatus. In particular, the measurement was conducted in a state in which the noise peak in the light scattering detector did not appear.

The calibration of the apparatus was conducted by using polyoxyethylene glycol (weight average molecular weight (Mw): 22396, molecular weight distribution (Mw/Mn=1.0), differential refractive index (dn/dc)=0.132, solvent refractive index: 1.33) as a standard sample. Further, the measurement was conducted by setting the differential refractive index (dn/dc) of the polymer as the analysis target to 0.132 and the solvent refractive index to 1.33.

The data collection and analysis of refractive index, light scattering intensity, and viscosity were conducted by Viscotek OmniSEC3.1 (registered trademark) software. The weight average molecular weight (Mw), the number average molecular weight (Mn), the molecular weight distribution (Mw/Mn), and the intrinsic viscosity (IV) were calculated from the refractive index (RI) and light scattering intensity (angle: 7°) LALS and the data obtained from the viscometer (DP). In the present specification, the intrinsic viscosity (IV) is synonymous with the limiting viscosity (IV).

<Weight Average Molecular Weight of Star-Shaped Polymers (1-$N_3$) to (4-$N_3$)>

The GPC measurement was conducted by using the following apparatus under the following conditions.

Apparatus for measurement: HLC-8120 (manufactured by Tosoh Corporation)

Column: two pieces of G5000HXL (manufactured by Tosoh Corporation) and GMHXL-L (manufactured by Tosoh Corporation) were used by being connected in series Eluent: tetrahydrofuran Standard substance for calibration curve: polystyrene Measuring method: the measurement target was dissolved in the eluent so as to have a solids content of 0.3 mass % and the solution thus obtained was filtered through a filter, and the obtained sample was subjected to the measurement. The measurement was conducted in a state in which the base line of the detector was stabilized by running a sufficient amount of the solvent through the apparatus.

Example 1

(Synthesis of Star-shaped Core with Four Arms)

A star-shaped core with four arms having the chemical structure represented by the following chemical formula A was synthesized by the method described in Scheme 1 (p. 14601) of a prior art literature (J. Am. Chem. Soc., 2006, 128, 14599-14605).

[Chem. 1]

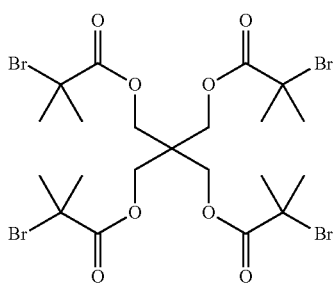

[Chemical formula A]

Star-shaped core with four arms (Synthesis of Star-shaped Polymer with Four Arms (1-Br))

In a 50 ml round-bottomed flask which was filled with nitrogen and in which a stirring bar was put, 80 mg of copper(I) bromide and 6 mg of copper(II) bromide were dissolved in 2.0 g of acetone and 14.1 g of tertiary butyl acrylate. Thereto, 107 mg of pentamethyldiethylenetriamine was added and the mixture was stirred for 5 minutes at room temperature, and 0.2 g of the star-shaped core with four arms synthesized above was added thereto, thereby preparing a reaction liquid. This reaction liquid was heated in an oil bath at 50° C. for 1.5 hours while stirring. The solution thus obtained was dried under reduced pressure at 1 mmHg for 5 hours at room temperature, thereby obtaining a crude product of the star-shaped polymer with four arms (1-Br) having the chemical structure represented by the following chemical formula B. A solution prepared by dissolving this crude product in 100 ml of diethyl ether was transferred to a separatory funnel, 100 ml of pure water was added thereto, and the mixture was shaken. The organic layer thus recovered was transferred to a separatory funnel, 100 ml of pure water was added thereto again, and the mixture was shaken. The organic layer thus obtained was dried under reduced pressure at 1 mmHg for 5 hours at room temperature, thereby obtaining the solid star-shaped polymer with four arms (1-Br). The chemical structure of the product thus obtained was confirmed by proton NMR measurement using heavy chloroform as a solvent. A characteristic peak includes the one which appears at the position of a chemical shift of 4.1 ppm, which is derived from hydrogen on the carbon having a bromine functional group.

[Chem. 2]

[Chemical formula B]

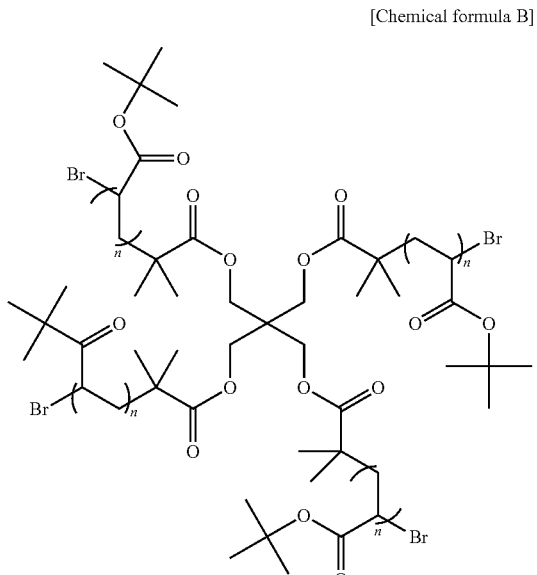

Star-shaped polymer with four arms (1-Br)
n = 20

[Chem. 3]

[Chemical formula C]

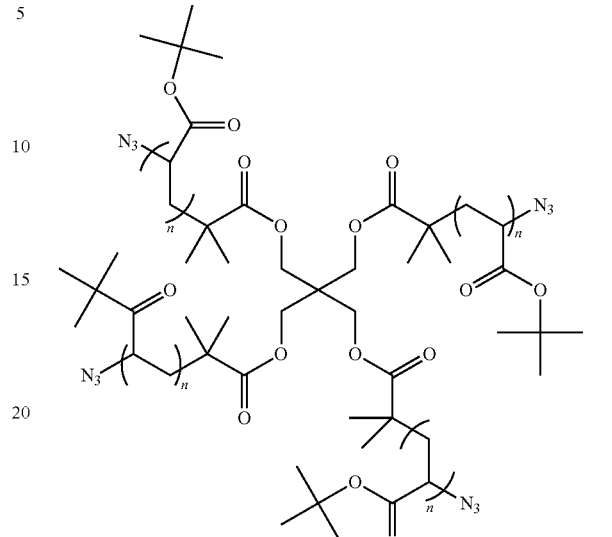

Star-shaped polymer with four arms (1-N₃)
n = 20

(Synthesis of Star-shaped Polymer with Four Arms (1-N₃))

In a 50 ml round-bottomed flask which was filled with nitrogen and in which a stirring bar was put, 2.0 g of the star-shaped polymer with four arms (1-Br) synthesized above and 156 mg of sodium azide were dissolved in 10 ml of dimethyl formamide, thereby preparing a reaction liquid. This reaction liquid was stirred for 18 hours at room temperature and dried under reduced pressure at 1 mmHg for 5 hours in a water bath at 50° C., thereby obtaining a crude product of the star-shaped polymer with four arms (1-N₃) having the chemical structure represented by the following chemical formula C. A solution prepared by dissolving this crude product in 100 ml of diethyl ether was transferred to a separatory funnel, 100 ml of pure water was added thereto, and the mixture was shaken. The organic layer thus recovered was transferred to a separatory funnel, 100 ml of pure water was added thereto again, and the mixture was shaken. The organic layer thus obtained was dried under reduced pressure at 1 mmHg for 5 hours at room temperature, thereby obtaining the solid star-shaped polymer with four arms (1-N₃). The chemical structure of the product thus obtained was confirmed by proton NMR measurement using heavy chloroform as a solvent. A characteristic peak includes the one which appears at the position of a chemical shift of 3.7 ppm, which is derived from hydrogen on the carbon having an azido functional group.

The weight average molecular weight Mw of the star-shaped polymer with four arms (1-N₃) obtained as described above was 12,550, and the molecular weight distribution Mw/Mn thereof was 1.15.

(Synthesis of dialkyne)

A dialkyne having the chemical structure represented by the following chemical formula D was obtained by the method described in a prior art literature (J. Am. Chem. Soc., 2007, 129, 12916-12917). Specifically, as described in the Supporting Information (S2) of the literature, a tetrahydrofuran solution of dimethyl 2-(propan-2-yl)malonate (1.0 mmol) was treated with NaH (1.5 mmol) at 0 C, the stirring thereof was continued for 30 minutes at room temperature, (3-bromo-1-propynyl)trimethylsilane (1.5 mmol) as an alkylating agent was then added thereto, and the reaction was allowed to proceed.

[Chem. 4]

[Chemical formula D]

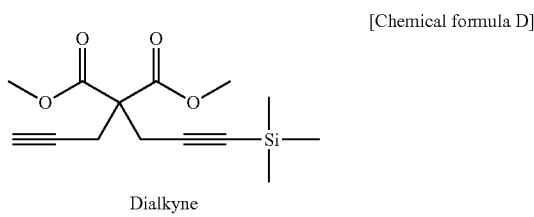

Dialkyne (Synthesis of Star-Shaped Polymer with Four Arms (1-Si Alkyne))

In a 50 ml round-bottomed flask which was filled with nitrogen and in which a stirring bar was put, 1.0 g of the star-shaped polymer with four arms (1-N₃) synthesized above, 134.6 mg of the dialkyne synthesized above, and 57.4 mg of copper (I) bromide were dissolved in 10 ml of dimethyl formamide. Thereto, 76.8 mg of pentamethyldiethylenetriamine was added, thereby preparing a reaction liquid. This reaction liquid was stirred for 18 hours at room temperature and dried under reduced pressure at 1 mmHg for 5 hours in a water bath at 50° C., thereby obtaining a crude product of the star-shaped polymer with four arms (1-Si alkyne) having a chemical structure represented by the following chemical formula E. A solution prepared by dissolving this crude product in 100 ml of diethyl ether was transferred to a separatory funnel, 100 ml of pure water was added thereto, and the mixture was shaken. The organic layer thus recovered was transferred to a separatory funnel, 100 ml of pure water was added thereto again, and the mixture was shaken. The organic layer thus obtained was dried under reduced pressure at 1 mmHg for 5 hours at room temperature, and the solid thus generated was washed with 50 ml of hexane three times, thereby obtaining the solid star-shaped polymer with four arms (1-Si alkyne). The chemical structure of the product thus obtained was confirmed by proton NMR measurement using heavy chloroform as a solvent. A characteristic peaks include the one which appears at the position of a chemical shift of 7.5 ppm, which is derived from hydrogen on the 1,2,3-triazole ring, the one which appears at the position of a chemical shift of 5.2 ppm, which is derived from hydrogen on the carbon having a 1,2,3-triazole ring, and the one which appears at the position of a chemical shift of 0.1 ppm, which is derived from hydrogen of the trimethylsilyl group.

was added, thereby preparing a reaction liquid. This reaction liquid was returned to room temperature, stirred for 18 hours, and dried under reduced pressure at 1 mmHg for 5 hours at room temperature, thereby obtaining a crude product of the star-shaped polymer with four arms (1-H alkyne) having a chemical structure represented by the following chemical formula F. A solution prepared by dissolving this crude product in 100 ml of diethyl ether was transferred to a separatory funnel, 100 ml of pure water was added thereto, and the mixture was shaken. The organic layer thus recovered was transferred to a separatory funnel, 100 ml of pure water was added thereto again, and the mixture was shaken. The organic layer thus obtained was dried under reduced pressure at 1 mmHg for 5 hours at room temperature, and the solid thus generated was washed with 50 ml of hexane three times, thereby obtaining the solid star-shaped polymer with four arms (1-H alkyne). The chemical structure of the product thus obtained was confirmed by proton NMR measurement using heavy chloroform as a solvent. In the same manner as the 1-Si alkyne described above, a peak derived

[Chem. 5]

[Chemical formula 5]

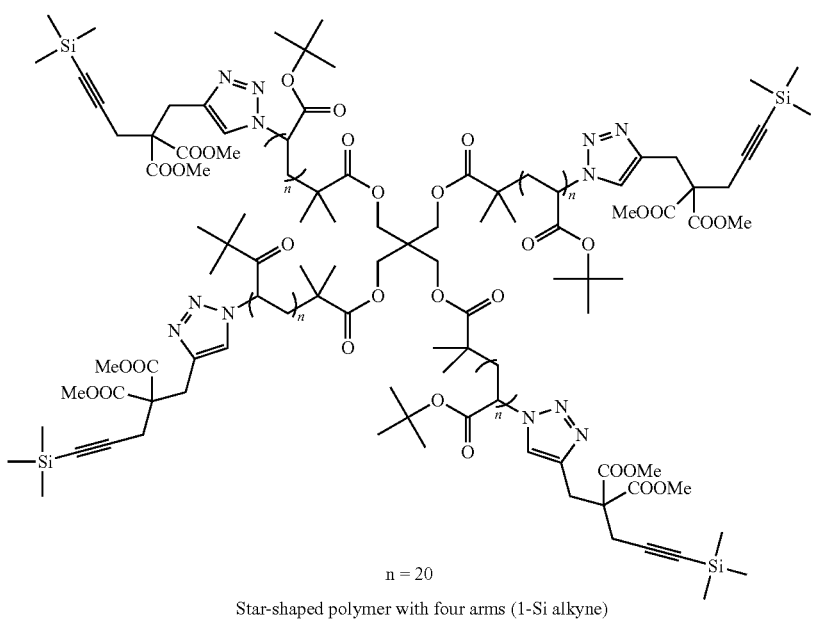

n = 20

Star-shaped polymer with four arms (1-Si alkyne)

(Synthesis of Star-Shaped Polymer with Four Arms (1-H Alkyne))

In a 50 ml round-bottomed flask which was filled with nitrogen and in which a stirring bar was put, 1.0 g of the star-shaped polymer with four arms (1-Si alkyne) synthesized above was dissolved in 10 ml of tetrahydrofuran, and the solution was cooled to 0° C. Thereto, 1.4 ml of a 1 mol/L tetrahydrofuran solution of tetrabutylammonium fluoride from hydrogen on the 1,2,3-triazole ring appeared at the position of a chemical shift of 7.5 ppm and a peak derived from hydrogen on the carbon having a 1,2,3-triazole ring appeared at the position of a chemical shift of 5.2 ppm as characteristic peaks. On the other hand, a peak did not appear at the position of a chemical shift of 0.1 ppm, and therefore the progress of the deprotection reaction of the trimethylsilyl group was confirmed.

[Chem. 6]

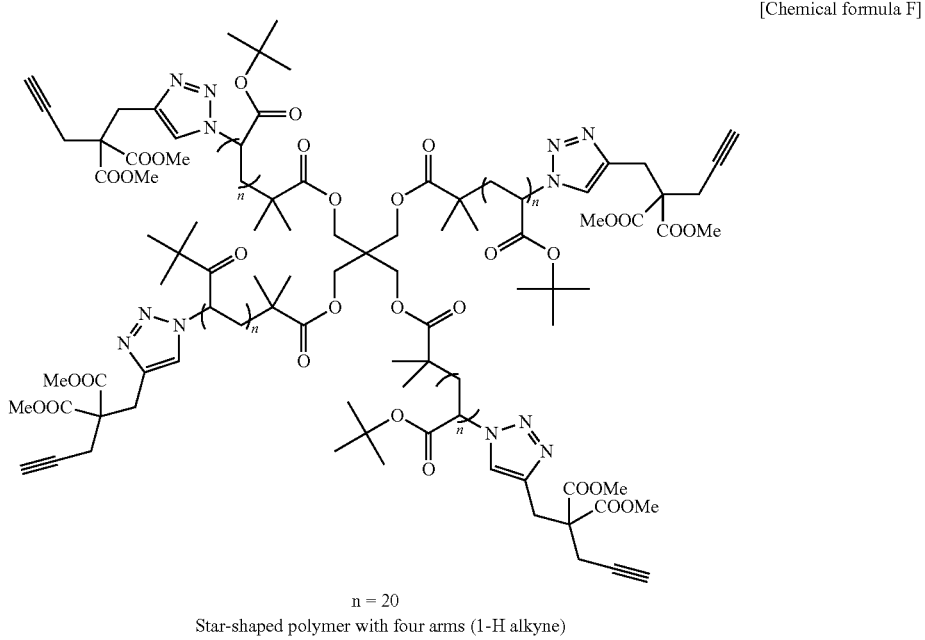

[Chemical formula F]

n = 20
Star-shaped polymer with four arms (1-H alkyne)

(Synthesis of Poly-Tert-Butyl Acrylate Crosslinked Body (1-tBA Gel))

In a glass vial which was filled with nitrogen and in which a stirring bar was put, 92.0 mg of the star-shaped polymer with four arms (1-$N_3$) synthesized above and 100.0 mg of the star-shaped polymer with four arms (1-H alkyne) synthesized above were dissolved in 533.0 µl of acetone, and the solution was cooled to 0° C. A solution prepared in a separate glass vial by dissolving 5.7 mg of copper(I) bromide and 7.7 mg of pentamethyldiethylenetriamine in 133.0 µl of methanol was added thereto, thereby preparing a reaction liquid. This reaction liquid was stirred for 30 seconds, the stirring bar was then taken out from the vial, the reaction liquid was left to stand still at room temperature, and the reaction liquid was solidified in about 30 minutes to be a gel. Thereafter, the glass vial was left to stand still for 18 hours at room temperature. The gel thus generated was taken out from the glass vial. In a 50 ml glass beaker, the gel thus obtained was immersed in 30 ml of acetone. This glass beaker was placed on a shaking table and shaken for 24 hours at a speed of 60 revolutions per minute to wash out the remaining copper. The acetone-swollen gel thus obtained was taken out from the glass beaker and dried for 24 hours at room temperature in the air, thereby obtaining the cylindrical poly-tert-butyl acrylate crosslinked body (1-tBA gel) having a chemical structure represented by the following chemical formula G.

[Chem. 7]

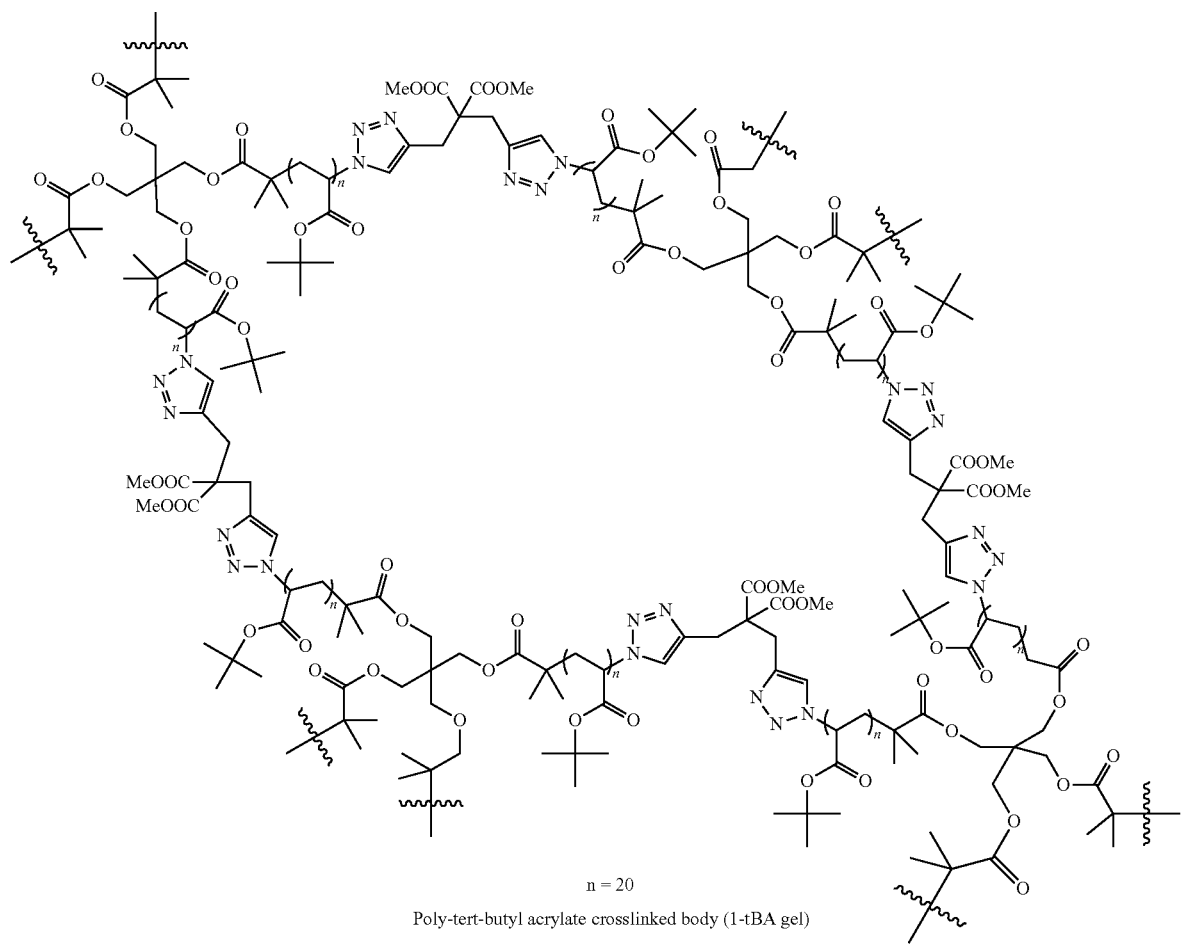

[Chemical formula G]

n = 20
Poly-tert-butyl acrylate crosslinked body (1-tBA gel)

(Synthesis of Water-Swollen Gel of Polyacrylic Acid Crosslinked Body (1-AA Gel))

To a 50 ml glass beaker, the poly-tert-butyl acrylate crosslinked body (1-tBA gel) synthesized above was transferred and immersed in a mixed liquid of 12 ml of dichloromethane and 3 ml of trifluoroacetic acid. This glass beaker was placed on a shaking table and shaken for 24 hours at a speed of 60 revolutions per minute. At this time, the crosslinked body once absorbed the mixture to swell, but contracted by discharging the mixed liquid again as the deprotection reaction of the tertiary butyl group by trifluoroacetic acid gradually proceeded. The polyacrylic acid crosslinked body generated by the deprotection reaction of the tertiary butyl group was taken out from the glass beaker and immersed in 30 ml of pure water in another 50 ml glass beaker. This glass beaker was placed on a shaking table and shaken for 18 hours at a speed of 60 revolutions per minute to wash out the remaining trifluoroacetic acid, thereby obtaining a water-swollen gel of the cylindrical polyacrylic acid crosslinked body (1-AA gel) having a chemical structure represented by the following chemical formula H.

[Chem. 8]

[Chemical formula H]

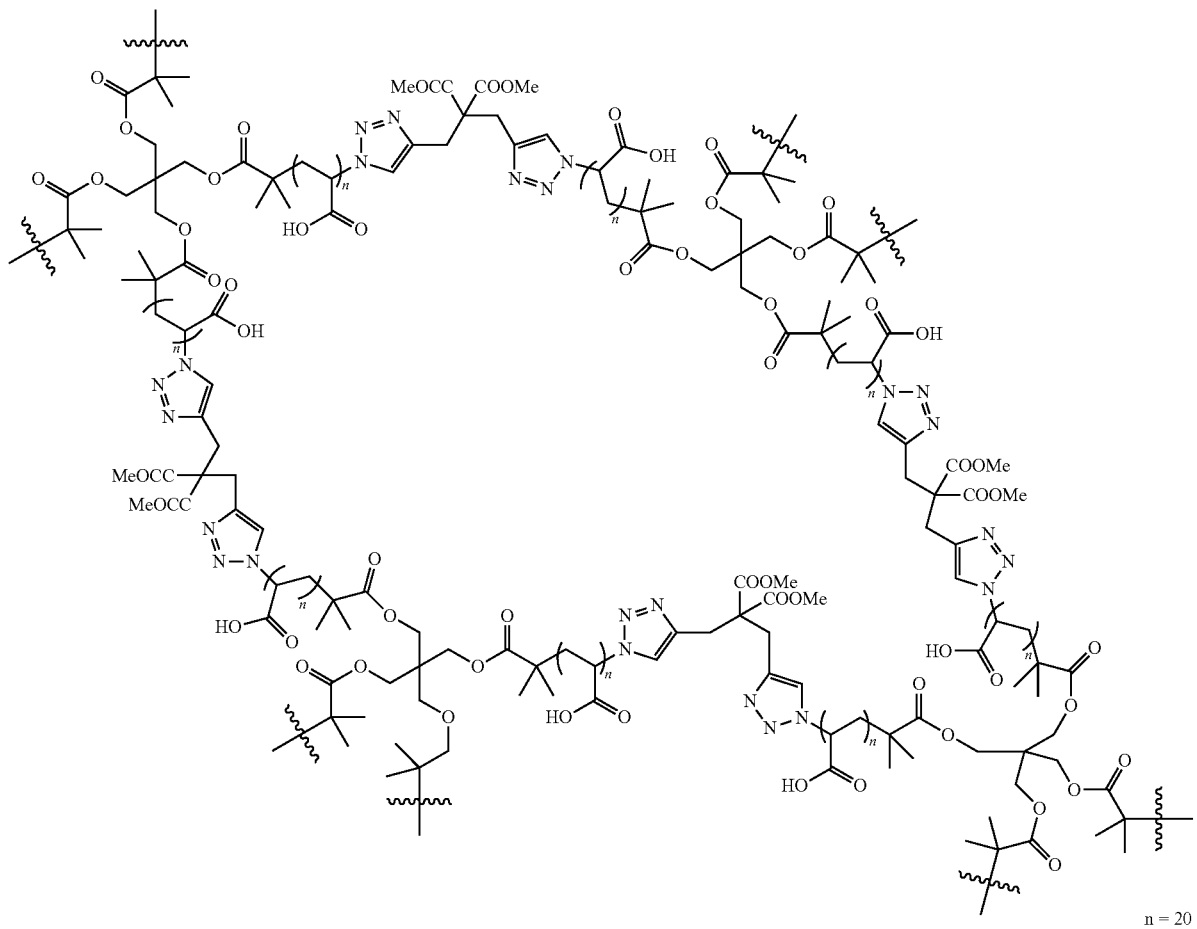

Water-swollen gel of polyacrylic acid crosslinked body (1-AA gel)

(Synthesis of Swollen Gel of Partially Neutralized Polyacrylic Acid Crosslinked Body (Water-Absorbing Resin 1) Having Reached Equilibrium Swollen State in 0.9 wt % Aqueous Sodium Chloride Solution)

In a 120 ml polypropylene container (manufactured by TGK), 94.5 mg of sodium hydrogen carbonate was dissolved in 30 ml of a 0.9 wt % aqueous sodium chloride solution, the water-swollen gel of the cylindrical polyacrylic acid crosslinked body (1-AA gel) synthesized above was immersed in this solution, and the container was left to stand still for 72 hours. The swollen gel of the partially neutralized polyacrylic acid crosslinked body (water-absorbing resin 1) thus obtained was transferred to a 250 ml polypropylene container and immersed in 200 ml of a 0.9 wt % aqueous sodium chloride solution, the container was left to stand still for 48 hours. Thereafter, the aqueous solution in the polypropylene container was removed, 200 ml of a 0.9 wt % aqueous sodium chloride solution was added into the container again, and the container was left to stand still for 48 hours. Thereafter, the aqueous solution in the polypropylene container was removed, 200 ml of a 0.9 wt % aqueous sodium chloride solution was added into the container again, and the container was left to stand still for 48 hours. In this manner, the swollen gel of a partially neutralized polyacrylic acid crosslinked body (water-absorbing resin 1) having reached an equilibrium swollen state in a 0.9 wt % aqueous sodium chloride solution was obtained. This swollen gel (water-absorbing resin 1) has the chemical structure represented by the following chemical formula I.

[Chem. 9]

[Chemical formula I]

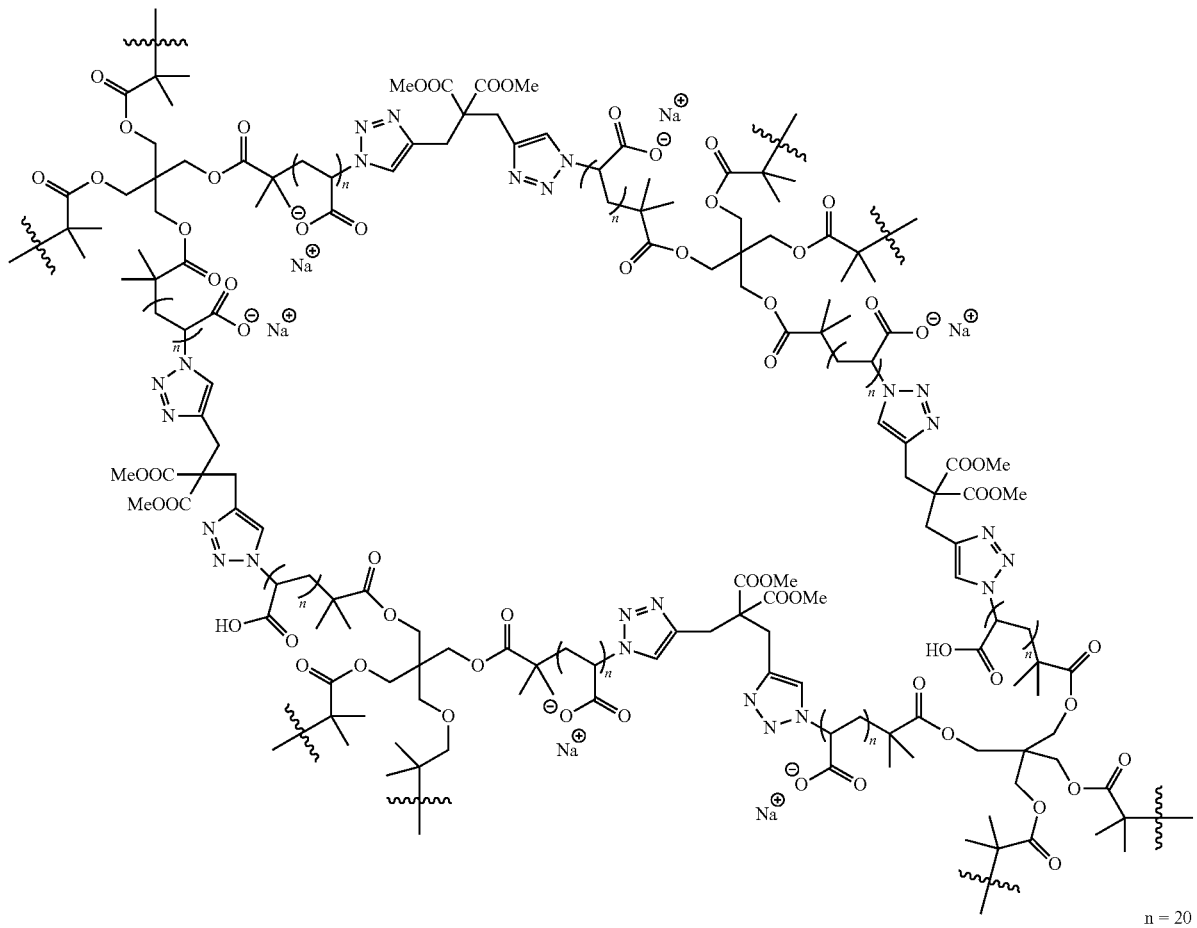

n = 20

Swollen gel of partially neutralized polyacrylic acid crosslinked body (water-absorbing resin 1) having reached equilibrium swollen state in 0.9 wt % aqueous sodium chloride solution The equilibrium swelling capacity of this swollen gel of a partially neutralized polyacrylic acid crosslinked body (water-absorbing resin 1) having reached an equilibrium swollen state in a 0.9 wt % aqueous sodium chloride solution was 24.8 g/g, and the elastic modulus thereof was 24, 276 Pa. The weight average molecular weight Mw thereof after a hydrolysis treatment was 7,355, and the molecular weight distribution Mw/Mn thereof was 1.06. These results are shown in the following Table 1. Further, a graph (origin is an equilibrium swelling capacity of 15 g/g and an elastic modulus of 300 Pa) plotted by taking the value of the equilibrium swelling capacity as the horizontal axis and the logarithm of the elastic modulus (Pa) as the vertical axis is shown in FIG. 1 (the same applies to the following Examples and Comparative Examples).

Example 2

(Synthesis of Star-shaped Polymer with Four Arms (2-Br))

The solid star-shaped polymer with four arms (2-Br) having the chemical structure represented by the above chemical formula B in which n=30 was obtained in the same manner as in the "Synthesis of star-shaped polymer with four arms (1-Br)" in Example 1 except that the amount of tertiary butyl acrylate was 17.6 g and the reaction time was 2 hours.

(Synthesis of Star-shaped Polymer with Four Arms (2-Na₃))

The star-shaped polymer with four arms (2-N₃) having the chemical structure represented by the above chemical formula C in which n=30 was obtained in the same manner as in the "Synthesis of star-shaped polymer with four arms (1-N₃)" in Example 1 except that the star-shaped polymer with four arms (2-Br) synthesized above was used instead of the star-shaped polymer with four arms (1-Br) and the amount of sodium azide (NaN₃) was 110 mg.

The weight average molecular weight Mw of the star-shaped polymer with four arms (2-N₃) obtained as described above was 17,029, and the molecular weight distribution Mw/Mn thereof was 1.11.

(Synthesis of Star-Shaped Polymer with Four Arms (2-Si Alkyne))

The solid star-shaped polymer with four arms (2-Si alkyne) having the chemical structure represented by the above chemical formula E in which n=30 was obtained in the same manner as in the "Synthesis of star-shaped polymer with four arms (1-Si alkyne)" in Example 1 except that the star-shaped polymer with four arms (2-$N_3$) synthesized above was used instead of the star-shaped polymer with four arms (1-$N_3$), the amount of the dialkyne was 89.7 mg, the amount of copper(I) bromide was 38.1 mg, and the amount of pentamethyldiethylenetriamine was 51.2 mg.

(Synthesis of Star-Shaped Polymer with Four Arms (2-H Alkyne))

The solid star-shaped polymer with four arms (2-H alkyne) having the chemical structure represented by the above chemical formula F in which n=30 was obtained in the same manner as in the "Synthesis of star-shaped polymer with four arms (1-H alkyne)" in Example 1 except that the star-shaped polymer with four arms (2-Si alkyne) synthesized above was used instead of the star-shaped polymer with four arms (1-Si alkyne) and the amount of the 1 mol/L tetrahydrofuran solution of tetrabutylammonium fluoride was 1.0 ml.

(Synthesis of Poly-Tert-Butyl Acrylate Crosslinked Body (2-tBA Gel))

The cylindrical poly-tert-butyl acrylate crosslinked body (2-tBA gel) having the chemical structure represented by the above chemical formula G in which n=30 was obtained in the same manner as in the "Synthesis of poly-tert-butyl acrylate crosslinked body (1-tBA gel)" in Example 1 except that 94.8 mg of the star-shaped polymer with four arms (2-$N_3$) synthesized above was used instead of 92.0 mg of the star-shaped polymer with four arms (1-$N_3$), the star-shaped polymer with four arms (2-H alkyne) synthesized above was used instead of the star-shaped polymer with four arms (1-H alkyne), the amount of copper(I) bromide was 3.8 mg, and the amount of pentamethyldiethylenetriamine was 4.8 mg.

(Synthesis of Water-Swollen Gel of Polyacrylic Acid Crosslinked Body (2-AA Gel))

The cylindrical water-swollen gel of a polyacrylic acid crosslinked body (2-AA gel) having the chemical structure represented by the above chemical formula H in which n=30 was obtained in the same manner as in the "Synthesis of water-swollen gel of polyacrylic acid crosslinked body (1-AA gel)" in Example 1 except that the poly-tert-butyl acrylate crosslinked body (2-tBA gel) synthesized above was used instead of the poly-tert-butyl acrylate crosslinked body (1-tBA gel).

(Synthesis of Swollen Gel (Water-Absorbing Resin 2) of Partially Neutralized Polyacrylic Acid Crosslinked Body Reached in Equilibrium Swollen State in 0.9 wt % Aqueous Sodium Chloride Solution)

The swollen gel of a partially neutralized polyacrylic acid crosslinked body (water-absorbing resin 2) having reached an equilibrium swollen state in a 0.9 wt % aqueous sodium chloride solution was obtained in the same manner as in the "Synthesis of swollen gel of partially neutralized polyacrylic acid crosslinked body (water-absorbing resin 1) having reached equilibrium swollen state in 0.9 wt % aqueous sodium chloride solution" in Example 1 except that the water-swollen gel of a polyacrylic acid crosslinked body (2-AA gel) was used instead of the water-swollen gel of a polyacrylic acid crosslinked body (1-AA gel). This swollen gel (water-absorbing resin 2) has the chemical structure represented by the above chemical formula I in which n=30.

The equilibrium swelling capacity of this swollen gel of a partially neutralized polyacrylic acid crosslinked body (water-absorbing resin 2) having reached an equilibrium swollen state in a 0.9 wt % aqueous sodium chloride solution was 38.4 g/g, and the elastic modulus thereof was 8,272 Pa. The weight average molecular weight Mw thereof after a hydrolysis treatment was 10,473, and the molecular weight distribution Mw/Mn thereof was 1.11. These results are shown in the following Table 1.

Example 3

(Synthesis of Star-shaped Polymer with Four Arms (3-Br))

The solid star-shaped polymer with four arms (3-Br) having the chemical structure represented by the above chemical formula B in which n=40 was obtained in the same manner as in the "Synthesis of star-shaped polymer with four arms (1-Br)" in Example 1 except that the amount of tertiary butyl acrylate was 28.2 g and the reaction time was 2 hours.

(Synthesis of Star-shaped Polymer with Four Arms (3-$N_3$))

The star-shaped polymer with four arms (3-$N_3$) having the chemical structure represented by the above chemical formula C in which n=40 was obtained in the same manner as in the "Synthesis of star-shaped polymer with four arms (1-$N_3$)" in Example 1 except that the star-shaped polymer with four arms (3-Br) was used instead of the star-shaped polymer with four arms (1-Br) and the amount of sodium azide (NaN$_3$) was 83 mg.

The weight average molecular weight Mw of the star-shaped polymer with four arms (3-$N_3$) obtained as described above was 25,585, and the molecular weight distribution Mw/Mn thereof was 1.11.

(Synthesis of Star-Shaped Polymer with Four Arms (3-Si Alkyne))

The solid star-shaped polymer with four arms (3-Si alkyne) having the chemical structure represented by the above chemical formula E in which n=40 was obtained in the same manner as in the "Synthesis of star-shaped polymer with four arms (1-Si alkyne)" in Example 1 except that the star-shaped polymer with four arms (3-$N_3$) was used instead of the star-shaped polymer with four arms (1-$N_3$), the amount of the dialkyne was 67.3 mg, the amount of copper (I) bromide was 28.6 mg, and the amount of pentamethyldiethylenetriamine was 38.4 mg.

(Synthesis of Star-Shaped Polymer with Four Arms (3-H Alkyne))

The solid star-shaped polymer with four arms (3-H alkyne) having the chemical structure represented by the above chemical formula F in which n=40 was obtained in the same manner as in the "Synthesis of star-shaped polymer with four arms (1-H alkyne)" in Example 1 except that the star-shaped polymer with four arms (3-Si alkyne) was used instead of the star-shaped polymer with four arms (1-Si alkyne) and the amount of the 1 mol/L tetrahydrofuran solution of tetrabutylammonium fluoride was 0.8 ml.

(Synthesis of Poly-Tert-Butyl Acrylate Crosslinked Body (3-tBA Gel))

The cylindrical poly-tert-butyl acrylate crosslinked body (3-tBA gel) having the chemical structure represented by the above chemical formula G in which n=40 was obtained in the same manner as in the "Synthesis of poly-tert-butyl acrylate crosslinked body (1-tBA gel)" in Example 1 except that 96.1 mg of the star-shaped polymer with four arms (3-$N_3$) was used instead of 92.0 mg of the star-shaped polymer with four arms (1-$N_3$), the star-shaped polymer with four arms (3-H alkyne) was used instead of the star-shaped polymer with four arms (1-H alkyne), the amount of copper(I) bromide was 3.0 mg, and the amount of pentamethyldiethylenetriamine was 3.6 mg.

(Synthesis of Water-Swollen Gel of Polyacrylic Acid Crosslinked Body (3-AA Gel))

The cylindrical water-swollen gel of a polyacrylic acid crosslinked body (3-AA gel) having the chemical structure represented by the above chemical formula H in which n=40 was obtained in the same manner as in the "Synthesis of water-swollen gel of polyacrylic acid crosslinked body (1-AA gel)" in Example 1 except that the poly-tert-butyl acrylate crosslinked body (3-tBA gel) was used instead of the poly-tert-butyl acrylate crosslinked body (1-tBA gel).

(Synthesis of Swollen Gel of Partially Neutralized Polyacrylic Acid Crosslinked Body (Water-Absorbing Resin 3) Having Reached Equilibrium Swollen State in 0.9 wt % Aqueous Sodium Chloride Solution)

The swollen gel of a partially neutralized polyacrylic acid crosslinked body (water-absorbing resin 3) having reached an equilibrium swollen state in a 0.9 wt % aqueous sodium chloride solution was obtained in the same manner as in the "Synthesis of swollen gel of partially neutralized polyacrylic acid crosslinked body (water-absorbing resin 1) having reached equilibrium swollen state in 0.9 wt % aqueous sodium chloride solution" in Example 1 except that the water-swollen gel of a polyacrylic acid crosslinked body (3-AA gel) was used instead of the water-swollen gel of a polyacrylic acid crosslinked body (1-AA gel). This swollen gel (water-absorbing resin 3) has the chemical structure represented by the above chemical formula I in which n=40.

The equilibrium swelling capacity of this swollen gel of a partially neutralized polyacrylic acid crosslinked body (water-absorbing resin 3) having reached an equilibrium swollen state in a 0.9 wt % aqueous sodium chloride solution was 42.5 g/g, and the elastic modulus thereof was 7,606 Pa. The weight average molecular weight Mw thereof after a hydrolysis treatment was 14,316, and the molecular weight distribution Mw/Mn thereof was 1.11. These results are shown in the following Table 1.

Example 4

(Synthesis of Star-shaped Polymer with Four Arms (4-Br))

The solid star-shaped polymer with four arms (4-Br) having the chemical structure represented by the above chemical formula B in which n=80 was obtained in the same manner as in the "Synthesis of star-shaped polymer with four arms (1-Br)" in Example 1 except that the amount of copper (I) bromide was 40 mg, the amount of copper (II) bromide was 3 mg, the amount of tertiary butyl acrylate was 28.2 g, the amount of pentamethyldiethylenetriamine was 54 mg, the amount of the star-shaped core with four arms was 0.1 g, and the reaction time was 2 hours.

(Synthesis of Star-shaped Polymer with Four Arms (4-$N_3$))

The star-shaped polymer with four arms (4-$N_3$) having the chemical structure represented by the above chemical formula C in which n=80 was obtained in the same manner as in the "Synthesis of star-shaped polymer with four arms (1-$N_3$)" in Example 1 except that the star-shaped polymer with four arms (4-Br) was used instead of the star-shaped polymer with four arms (1-Br) and the amount of sodium azide (Na$N_3$) was 41 mg.

The weight average molecular weight Mw of the star-shaped polymer with four arms (4-$N_3$) obtained as described above was 45,728, and the molecular weight distribution Mw/Mn thereof was 1.16.

(Synthesis of Star-Shaped Polymer with Four Arms (4-Si Alkyne))

The solid star-shaped polymer with four arms (4-Si alkyne) having the chemical structure represented by the above chemical formula E in which n=80 was obtained in the same manner as in the "Synthesis of star-shaped polymer with four arms (1-Si alkyne)" in Example 1 except that the star-shaped polymer with four arms (4-$N_3$) was used instead of the star-shaped polymer with four arms (1-$N_3$), the amount of the dialkyne was 33.6 mg, the amount of copper (I) bromide was 14.3 mg, and the amount of pentamethyl-diethylenetriamine was 19.2 mg.

(Synthesis of Star-shaped Polymer with Four Arms (4-H Alkyne))

The solid star-shaped polymer with four arms (4-H alkyne) having the chemical structure represented by the above chemical formula F in which n=80 was obtained in the same manner as in the "Synthesis of star-shaped polymer with four arms (1-H alkyne)" in Example 1 except that the star-shaped polymer with four arms (4-Si alkyne) was used instead of the star-shaped polymer with four arms (1-Si alkyne) and the amount of the 1 mol/L tetrahydrofuran solution of tetrabutylammonium fluoride was 0.4 ml.

(Synthesis of Poly-tert-butyl Acrylate Crosslinked Body (4-tBA Gel))

The cylindrical poly-tert-butyl acrylate crosslinked body (4-tBA gel) having the chemical structure represented by the above chemical formula G in which n=80 was obtained in the same manner as in the "Synthesis of poly-tert-butyl acrylate crosslinked body (1-tBA gel)" in Example 1 except that 98.0 mg of the star-shaped polymer with four arms (4-$N_3$) was used instead of 92.0 mg of the star-shaped polymer with four arms (1-$N_3$), the star-shaped polymer with four arms (4-H alkyne) was used instead of the star-shaped polymer with four arms (1-H alkyne), the amount of copper(I) bromide was 1.5 mg, and the amount of pentamethyldiethylenetriamine was 1.8 mg.

(Synthesis of Water-swollen Gel of Polyacrylic Acid Crosslinked Body (4-AA Gel))

The cylindrical water-swollen gel of a polyacrylic acid crosslinked body (4-AA gel) having the chemical structure represented by the above chemical formula H in which n=80 was obtained in the same manner as in the "Synthesis of water-swollen gel of polyacrylic acid crosslinked body (1-AA gel)" in Example 1 except that the poly-tert-butyl acrylate crosslinked body (4-tBA gel) was used instead of the poly-tert-butyl acrylate crosslinked body (1-tBA gel).

(Synthesis of Swollen Gel of Partially Neutralized Polyacrylic Acid Crosslinked Body (Water-absorbing Resin 4) Having Reached Equilibrium Swollen State in 0.9 wt % Aqueous Sodium Chloride Solution)

The swollen gel of a partially neutralized polyacrylic acid crosslinked body (water-absorbing resin 4) having reached an equilibrium swollen state in a 0.9 wt % aqueous sodium chloride solution was obtained in the same manner as in the "Synthesis of swollen gel of partially neutralized polyacrylic acid crosslinked body (water-absorbing resin 1) having reached equilibrium swollen state in 0.9 wt % aqueous sodium chloride solution" in Example 1 except that the water-swollen gel of a polyacrylic acid crosslinked body (4-AA gel) was used instead of the water-swollen gel of a polyacrylic acid crosslinked body (1-AA gel). This swollen gel (water-absorbing resin 4) has the chemical structure represented by the above chemical formula I in which n=80.

The equilibrium swelling capacity of this swollen gel of a partially neutralized polyacrylic acid crosslinked body (water-absorbing resin 4) having reached an equilibrium swollen state in a 0.9 wt % aqueous sodium chloride solution was 80.4 g/g, and the elastic modulus thereof was 1,308 Pa. The weight average molecular weight Mw thereof after a hydrolysis treatment was 24, 725, and the molecular weight distribution Mw/Mn thereof was 1.14. These results are shown in the following Table 1.

Comparative Example 1

In a polypropylene container having a capacity of 250 ml (manufactured by TGK), 17.170 g of a 48 mass % aqueous sodium hydroxide solution and 21.750 g of pure water cooled to 5° C. were put, and the mixture was stirred. Thereto, a mixture of 0.144 g of polyethylene glycol diacrylate (molecular weight (Mw): 523) and 19.800 g of acrylic acid was gradually added, thereby preparing a reaction liquid. Next, this reaction liquid was degassed for 20 minutes in a nitrogen gas atmosphere. Subsequently, 0.650 g of a 10 mass % aqueous sodium persulfate solution and 0.484 g of a 0.1 mass % aqueous L-ascorbic acid solution were added to the reaction liquid while stirring. The reaction liquid thus obtained was quickly transferred by using a syringe to the following reaction vessel purged with nitrogen gas and left to stand still for 18 hours in a dryer at 60° C., thereby obtaining a disk-shaped gel. The reaction vessel was formed by sandwiching silicone rubber having circular holes between two glass plates and fastening the periphery thereof with clips.

A part (2.0 g) of this gel was cut into a strip shape, transferred to a polypropylene container with lid having a capacity of 780 ml (manufactured by ENTECH CO., LTD.), immersed in 400 ml of a 0.9 wt % aqueous sodium chloride solution, and left to stand still for 48 hours. Thereafter, the aqueous solution in the polypropylene container was removed, 400 ml of a 0.9 wt % aqueous sodium chloride solution was added into the container again, and the container was left to stand still for 48 hours. Thereafter, the aqueous solution in the polypropylene container was removed, 400 ml of a 0.9 wt % aqueous sodium chloride solution was added into the container again, and the container was left to stand still for 48 hours. In this manner, the swollen gel of a partially neutralized polyacrylic acid crosslinked body (comparative water-absorbing resin 1) of the present Comparative Example having reached an equilibrium swollen state in a 0.9 wt % aqueous sodium chloride solution was obtained.

The equilibrium swelling capacity of this swollen gel of a partially neutralized polyacrylic acid crosslinked body (comparative water-absorbing resin 1) of the present Comparative Example having reached an equilibrium swollen state in a 0.9 wt % t aqueous sodium chloride solution was 33.5 g/g, and the elastic modulus thereof was 7,867 Pa. The weight average molecular weight Mw thereof after a hydrolysis treatment was 1,460,000, and the molecular weight distribution (Mw/Mn) thereof was 1.69. These results are shown in the following Table 1.

Comparative Example 2

The swollen gel of a partially neutralized polyacrylic acid crosslinked body (comparative water-absorbing resin 2) of the present Comparative Example having reached an equilibrium swollen state in a 0.9 wt % aqueous sodium chloride solution was obtained in the same manner as in Comparative Example 1 except that the amount of polyethylene glycol diacrylate was 0.058 g and the amount of pure water was 21.836 g.

The equilibrium swelling capacity of this swollen gel of a partially neutralized polyacrylic acid crosslinked body (comparative water-absorbing resin 2) of the present Comparative Example having reached an equilibrium swollen state in a 0.9 wt % aqueous sodium chloride solution was 37.3 g/g, and the elastic modulus thereof was 5,910 Pa. The weight average molecular weight Mw thereof after a hydrolysis treatment was 1,370,000, and the molecular weight distribution (Mw/Mn) thereof was 1.56. These results are shown in the following Table 1.

Comparative Example 3

The swollen gel of a partially neutralized polyacrylic acid crosslinked body (comparative water-absorbing resin 3) of the present Comparative Example having reached an equilibrium swollen state in a 0.9 wt % aqueous sodium chloride solution was obtained in the same manner as in Comparative Example 1 except that the amount of polyethylene glycol diacrylate was 0.043 g and the amount of pure water was 21.851 g.

The equilibrium swelling capacity of this swollen gel of a partially neutralized polyacrylic acid crosslinked body (comparative water-absorbing resin 3) of the present Comparative Example having reached an equilibrium swollen state in a 0.9 wt % aqueous sodium chloride solution was 44.5 g/g, and the elastic modulus thereof was 3,541 Pa. The weight average molecular weight Mw thereof after a hydrolysis treatment was 1,440,000, and the molecular weight distribution (Mw/Mn) thereof was 1.52. These results are shown in the following Table 1.

Comparative Example 4

The swollen gel of a partially neutralized polyacrylic acid crosslinked body (comparative water-absorbing resin 4) of the present Comparative Example having reached an equilibrium swollen state in a 0.9 wt % aqueous sodium chloride solution was obtained in the same manner as in Comparative Example 1 except that the amount of polyethylene glycol diacrylate was 0.028 g and the amount of pure water was 21.866 g.

The equilibrium swelling capacity of this swollen gel of a partially neutralized polyacrylic acid crosslinked body (comparative water-absorbing resin 4) of the present Comparative Example in an equilibrium swollen state in a 0.9 wt % aqueous sodium chloride solution was 65.5 g/g, and the elastic modulus thereof was 980 Pa. The weight average molecular weight Mw thereof after a hydrolysis treatment was 1,340,000, and the molecular weight distribution (Mw/Mn) thereof was 1.56. These results are shown in the following Table 1.

Comparative Example 5

The swollen gel of a partially neutralized polyacrylic acid crosslinked body (comparative water-absorbing resin 5) of the present Comparative Example having reached an equilibrium swollen state in a 0.9 wt % aqueous sodium chloride solution was obtained in the same manner as in Comparative Example 1 except that the amount of a 10 mass % aqueous sodium persulfate solution was 3.250 g, the amount of a 0.1 mass % aqueous L-ascorbic acid solution was 2.420 g, and the amount of pure water was 17.170 g.

The equilibrium swelling capacity of this swollen gel of a partially neutralized polyacrylic acid crosslinked body (comparative water-absorbing resin 5) of the present Comparative Example having reached an equilibrium swollen state in a 0.9 wt % aqueous sodium chloride solution was 31.7 g/g, and the elastic modulus thereof was 9,328 Pa. The weight average molecular weight Mw thereof after a hydrolysis treatment was 927, 682, and the molecular weight distribution (Mw/Mn) thereof was 1.85. These results are shown in the following Table 1.

Comparative Example 6

The swollen gel of a partially neutralized polyacrylic acid crosslinked body (comparative water-absorbing resin 6) of the present Comparative Example in an equilibrium swollen state in a 0.9 wt % aqueous sodium chloride solution was obtained in the same manner as in Comparative Example 1 except that the amount of pure water was 17.170 g and 2.970 g of a 10 mass % aqueous disodium hydrogen phosphite pentahydrate solution was simultaneously added with the 10 mass % aqueous sodium persulfate solution and the 0.1 mass % aqueous L-ascorbic acid solution.

The equilibrium swelling capacity of this swollen gel of a partially neutralized polyacrylic acid crosslinked body (comparative water-absorbing resin 6) of the present Comparative Example having reached an equilibrium swollen state in a 0.9 wt % aqueous sodium chloride solution was 33.1 g/g, and the elastic modulus thereof was 8,421 Pa. The weight average molecular weight Mw thereof after a hydrolysis treatment was 1,116,000, and the molecular weight distribution (Mw/Mn) thereof was 1.49. These results are shown in the following Table 1.

Comparative Example 7

In a polypropylene container having a capacity of 120 ml, 20.00 g of a 30 mass % aqueous sodium polyacrylate solution (DL522 manufactured by NIPPON SHOKUBAI CO., LTD.) was added to 0.111 g of ethylene glycol diglycidyl ether (Denacol EX-810 manufactured by Nagase ChemteX Corporation) and dissolved by stirring with a spatula. Thereafter, the pack ace was capped, the container was left to stand still for 3 hours to eliminate the bubbles in the solution. This polypropylene container was put in an oven at 80° C. and left to stand still for 12 hours, thereby obtaining a disk-shaped gel.

This gel was transferred to a polypropylene container with lid having a capacity of 780 ml (manufactured by ENTECH CO., LTD.), immersed in a mixed liquid of 8 ml of a 2 mol/l aqueous hydrochloric acid solution and 192 ml of a 0.9 wt % aqueous sodium chloride solution, and left to stand still for 72 hours. Thereafter, the aqueous solution in the polypropylene container was removed, 200 ml of a 0.9 wt % aqueous sodium chloride solution was added into the container, and the container was left to stand still for 48 hours. Thereafter, the aqueous solution in the polypropylene container was removed, 200 ml of a 0.9 wt % aqueous sodium chloride solution was added into the container again, and the container was left to stand still for 48 hours. Once more, the aqueous solution in the polypropylene container was removed, 200 ml of a 0.9 wt % aqueous sodium chloride solution was added into the container again, and the container was left to stand still for 48 hours. In this manner, the swollen gel of a partially neutralized polyacrylic acid crosslinked body (comparative water-absorbing resin 7) of the present Comparative Example having reached an equilibrium swollen state in a 0.9 wt % aqueous sodium chloride solution was obtained.

The equilibrium swelling capacity of this swollen gel of a partially neutralized polyacrylic acid crosslinked body (comparative water-absorbing resin 7) of the present Comparative Example having reached an equilibrium swollen state in a 0.9 wt % aqueous sodium chloride solution was 51.8 g/g, and the elastic modulus thereof was 3,149 Pa. The weight average molecular weight Mw thereof after a hydrolysis treatment was 239,600, and the molecular weight distribution (Mw/Mn) thereof was 3.48. These results are shown in the following Table 1.

Comparative Example 8

In Examples and Comparative Examples of JP 2009-531467 W, which is one of the prior art literatures described above, CRC and weight average molecular weight (Mw) after a hydrolysis treatment of various water-absorbing resins are described. Among these, for the water-absorbing resin having the highest "reference crosslinked structure index" expressed by the following numerical formula 2, CRC is 28.3 (g/g), weight-average molecular weight (Mw) after a hydrolysis treatment is 221,634, and molecular weight distribution (Mw/Mn) is 1.95. This water-absorbing resin is adopted as the comparative water-absorbing resin 8, and these results are shown in the following Table 1.

[Math. 3]

$$\text{Reference crosslinked structure index} = (CRC)^{1/3} / (\text{Weight average molecular weight (Mw) after hydrolysis treatment}) \times 1000000 \quad \text{[Numerical formula 2]}$$

TABLE 1

| | Water-absorbing resin | Weight average molecular weight after hydrolysis treatment Mw | Molecular weight distribution after hydrolysis treatment Mw/Mn | Equilibrium swelling capacity with respect to 0.9 wt % physiological saline solution (g/g) | Elastic modulus (Pa) | Crosslinked structure index |
|---|---|---|---|---|---|---|
| Example 1 | Water-absorbing resin 1 | 7,355 | 1.06 | 24.8 | 24,276 | 397.58 |
| Example 2 | Water-absorbing resin 2 | 10,473 | 1.11 | 38.4 | 8,272 | 322.14 |
| Example 3 | Water-absorbing resin 3 | 14,316 | 1.11 | 42.5 | 7,606 | 243.77 |
| Example 4 | Water-absorbing resin 4 | 24,725 | 1.14 | 80.4 | 1,308 | 174.56 |
| Comparative Example 1 | Comparative water-absorbing resin 1 | 1,460,000 | 1.69 | 33.5 | 7,867 | 2.21 |

TABLE 1-continued

| Water-absorbing resin | Weight average molecular weight after hydrolysis treatment Mw | Molecular weight distribution after hydrolysis treatment Mw/Mn | Equilibrium swelling capacity with respect to 0.9 wt % physiological saline solution (g/g) | Elastic modulus (Pa) | Crosslinked structure index |
|---|---|---|---|---|---|
| Comparative Example 2 — Comparative water-absorbing resin 2 | 1,370,000 | 1.56 | 37.3 | 5,910 | 2.44 |
| Comparative Example 3 — Comparative water-absorbing resin 3 | 1,440,000 | 1.52 | 44.5 | 3,541 | 2.46 |
| Comparative Example 4 — Comparative water-absorbing resin 4 | 1,340,000 | 1.56 | 65.5 | 980 | 3.01 |
| Comparative Example 5 — Comparative water-absorbing resin 5 | 927,682 | 1.85 | 31.7 | 9,328 | 3.41 |
| Comparative Example 6 — Comparative water-absorbing resin 6 | 1,116,000 | 1.49 | 33.1 | 8,421 | 2.88 |
| Comparative Example 7 — Comparative water-absorbing resin 7 | 239,600 | 3.48 | 51.8 | 3,149 | 15.56 |
| Comparative Example 8 — Comparative water-absorbing resin 8 | 221,634 | 1.95 | 28.3*[1] | — | 13.75*[2] |

*[1] It is not the equilibrium swelling capacity with respect to 0.9 wt % physiological saline solution but CRC.
*[2] It is not the crosslinked structure index but the reference crosslinked structure index.

From the results shown in Table 1 and FIG. 1, it can be seen that the water-absorbing resins of Examples 1 to 4 according to the present invention have a higher swollen gel elastic modulus as compared to the water-absorbing resins according to Comparative Examples which have an equal equilibrium swelling capacity with those of Examples 1 to 4. Further, it can be seen that the crosslinked structure index decreases as the weight average molecular weight (Mw) of the water-absorbing resins after a hydrolysis treatment increases in Examples 1 to 4. It is considered that a water-absorbing resin synthesized in accordance with the same procedure as in Examples 1 to 4 and by using a star-shaped polymer having a reactive functional group at the terminal and an even greater molecular weight as a starting material has an even greater weight average molecular weight (Mw) after a hydrolysis treatment and a smaller crosslinked structure index. It is considered that the water-absorbing resin thus obtained also has fewer entanglements and dangling chains in the same manner as in Examples 1 to 4 and a higher swollen gel elastic modulus as compared to the water-absorbing resins according to Comparative Examples which have an equal equilibrium swelling capacity with these water-absorbing resin. That is, it is considered that it is also possible to obtain a water-absorbing resin having a higher weight average molecular weight (Mw) after a hydrolysis treatment and a smaller crosslinked structure index than those according to Examples 1 to 4 and a higher swollen gel elastic modulus as compared to the water-absorbing resins according to Comparative Examples which have an equal equilibrium swelling capacity with these water-absorbing resin.

Taking these into consideration, it can be expected that, when a water-absorbing resin has a value of the crosslinked structure index of 14 or more (preferably 170 or more), a weight average molecular weight (Mw) after a hydrolysis treatment of 220,000 or less, and a molecular weight distribution (Mw/Mn) of 3.40 or less, the water-absorbing resin has a higher swollen gel elastic modulus as compared to the water-absorbing resins according to Comparative Examples which have an equal equilibrium swelling capacity with the water-absorbing resin. From this, it can be said that the water-absorbing resin according to the present invention exhibits superior liquid permeability even under a load as compared to a water-absorbing resin formed from a partially neutralized polyacrylic acid (salt) crosslinked body of the prior art.

This application is based upon the prior Japanese Patent Application No. 2014-127897 filed on Jun. 23, 2014 and the prior Japanese Patent Application No. 2014-174584 filed on Aug. 28, 2014, the entire contents of which are incorporated herein by reference.

The invention claimed is:

1. A water-absorbing resin comprising a water soluble unsaturated monomer having a dissociable group as a main component of a repeating unit of a main chain, wherein
the water-absorbing resin has an internal crosslinked structure,
a crosslinked structure index expressed by the following numerical formula 1 is 14 or more,
a weight average molecular weight (Mw) of the water-absorbing resin after a hydrolysis treatment is 220,000 or less, and
a molecular weight distribution (Mw/Mn) of the water-absorbing resin after a hydrolysis treatment is 1.00 or more and 3.40 or less:

[Math. 1]

$$\text{Crosslinked structure index} = \frac{(\text{Equilibrium swelling capacity with respect to 0.9 wt \% physiological saline solution})^{1/3}}{\text{Weight average molecular weight (Mw) after hydrolysis treatment}} \times 1000000 \quad \text{[Numerical formula 1]}$$

where the hydrolysis treatment is a treatment to leave 50 mg of the water-absorbing resin as a solids content to stand still in 10 g of a 0.1 mol/l aqueous sodium hydroxide solution for 3 weeks at 80° C., and the weight average molecular weight (Mw) is a value measured after the treatment.

2. The water-absorbing resin according to claim 1, wherein 90 mol % or more of the repeating unit is a repeating unit derived from a water soluble unsaturated monomer having a carboxylic acid (salt) group as a dissociable group.

3. The water-absorbing resin according to claim 1, wherein 90 mol % or more of the repeating unit is a repeating unit derived from acrylic acid (salt).

4. The water-absorbing resin according to claim 1, wherein a rate of neutralization of the water-absorbing resin is from 50 to 100 mol %.

5. A method for producing a water-absorbing resin comprising a water soluble unsaturated monomer having a dissociable group as a main component of a repeating unit of a main chain and having an internal crosslinked structure, the method comprising:
a reaction step for reacting a first star-shaped polymer comprising the water soluble unsaturated monomer as a main component of a repeating unit of each branched chain and having a first reactive functional group at a terminal of each branched chain with
a second star-shaped polymer comprising the water soluble unsaturated monomer as a main component of a repeating unit of each branched chain and having a second reactive functional group capable of forming a chemical bond with the first reactive functional group by reacting with each other at a terminal of each branched chain.

6. The method according to claim 5, wherein 90 mol % or more of the repeating unit of the branched chain is a repeating unit derived from acrylic acid (salt) in each of the first star-shaped polymer and the second star-shaped polymer.

7. The method according to claim 5, wherein the first star-shaped polymer and the second star-shaped polymer have a structure in which a polymer comprising the water soluble unsaturated monomer as a main component of a repeating unit is bonded to a core with four arms as a branched chain.

8. The method according to claim 5, wherein the first reactive functional group is an azido group and the second reactive functional group is an alkynyl group.

9. The method according to claim 5, wherein the reaction step is carried out in a state of protecting the dissociable group in the water soluble unsaturated monomer constituting the branched chains of the first star-shaped polymer and the second star-shaped polymer with a protecting group, and
the method further comprises a step for de-protecting the dissociable group after the reaction step is completed.

10. The method according to claim 5, further comprising a step for neutralizing the dissociable group.

* * * * *